(12) United States Patent
Novak et al.

(10) Patent No.: US 8,334,280 B2
(45) Date of Patent: Dec. 18, 2012

(54) LIGANDS OF ESTROGEN RECEPTORS α AND β, METHOD OF THEIR PREPARATION, AND PHARMACEUTICALS COMPRISING THEM

(75) Inventors: Petr Novak, Havlichkuv Brod (CZ); David Sedlak, Praha (CZ); Petr Bartunek, Praha (CZ); Martin Kotora, Praha (CZ)

(73) Assignees: Ustav Molekularni Genetikv AV CR, V.V.I. (CZ); Ustav Organicke Chemie A Biochemie AV CR, V.V.I. (CZ); Univerzita Karlova V Praze, Prirodovedecka Fukulta UK (CZ)

( * ) Notice: Subject to any disclaimer, the term of this patent is extended or adjusted under 35 U.S.C. 154(b) by 83 days.

(21) Appl. No.: 12/990,826

(22) PCT Filed: May 5, 2009

(86) PCT No.: PCT/CZ2009/000066
§ 371 (c)(1),
(2), (4) Date: Jan. 24, 2011

(87) PCT Pub. No.: WO2009/135449
PCT Pub. Date: Nov. 12, 2009

(65) Prior Publication Data
US 2011/0118225 A1 May 19, 2011

(30) Foreign Application Priority Data
May 5, 2008 (CV) .................................. PV2008-275

(51) Int. Cl.
*A61K 31/567* (2006.01)
*A61K 31/58* (2006.01)
*C07J 1/00* (2006.01)
*C07J 17/00* (2006.01)
*C07J 43/00* (2006.01)

(52) U.S. Cl. .......... 514/182; 514/172; 514/176; 540/94; 540/95; 552/630

(58) Field of Classification Search .................. 552/630; 540/94, 95; 514/182, 172, 176
See application file for complete search history.

(56) References Cited

U.S. PATENT DOCUMENTS

| 2004/0056191 A1 | 3/2004 | Jenkins et al. |
| 2007/0135400 A1 | 6/2007 | Agoston et al. |

FOREIGN PATENT DOCUMENTS

| EP | 0 345 153 A1 | 5/1989 |
| EP | 1 131 336 B1 | 11/1999 |
| GB | 2 361 642 A | 10/2001 |
| WO | 0053620 | 9/2000 |
| WO | 2005048956 A2 | 6/2005 |
| WO | 2005099704 A1 | 10/2005 |
| WO | 2006013196 A1 | 2/2006 |

OTHER PUBLICATIONS

Grodstein, F., Newcomb, P.A. & Stampfer, M.J. "Postmenopausal hormone therapy and the risk of colorectal cancer: A review and meta-analysis." Am J Med, 106, 574-82 (1999).
Campbell-Thompson, M., Lynch, I.J. & Bhardwaj, B. "Expression of estrogen receptor (ER) subtypes and ERbeta isoforms in colon cancer." Cancer Res, 61, 632-40 (2001).
Stephan, E., Affergan, T., Weber, P. & Jaquen, G. "Boron Trifluoride Promoted Addition of Aryllithiums to Estrone Benzyl Ether." Tetrahedron Lett., 39, 9427-9430 (1998).
Foy, N., Stephan, E. & Jaquen, G. "Synthesis of 17 α-4-amino- and 4-iodophenylestradiols." Tetrahedron Lett., 41, 8089-8092 (2000).
Foy, N. et al. "Synthesis, receptor binding, molecular modeling, and proliferative essays of a series of 17 alpha-arylestradiols." Chembiochem, 4, 494-503 (2003).
Peters, Richard H. et al. "17-Desoxy Estrogen Analogues." Am Chem Soc, 32, 1642-52 (1989).
Salman, Mohammad et al. "17α-Substituted analogs of estradiol for the development of fluorescent estrogen receptor ligands."
Amouri, Hani El et al. "Syntheses and affinities of novel organometallic-labeled estradiol derivatives: A structure-affinity relationship." J Med Chem, 35, 3130-35 (1992).
Napolitano, Elio et al. "11β-Substituted estradiol derivatives, potential high-affinity carbon-11-labeled probes for the estrogen receptor: A structure-affinity relationship study." J Med Chem, 38, 429-34 (1995).
Chalabala, M. et al. Technologie Leku (Technology of Medicaments) Galen, Praha, 2001. ISBN 8072621289. (Book cover and plate only).
Kibbe, A.H. "Handbook of Pharmaceutical Excipients." Pharmaceutical Press, London, 2000. ISBN 091733096. (no attachment).
International Search Report from PCT/CZ2009/000066 issued Oct. 16, 2009.
Green, G.L.et al. "Sequence and expression of human estrogen receptor complementary DNA." Science, 231, 1150-4 (1986).
Green, S. et al. "Human oestrogen receptor cDNA: Sequence, expression and homology to verb-A." Nature, 320, 134-9 (1986).

(Continued)

*Primary Examiner* — Barbara P Badio
(74) *Attorney, Agent, or Firm* — Reinhart Boerner Van Deuren s.c.

(57) ABSTRACT

The invention relates to novel ligands of the estrogen receptors α and β of general formula II, which are useful as an active substance of pharmaceuticals, for example pharmaceutical compositions useful for hormone replacement therapy, as well as for the treatment of tumors and inflammatory diseases. The invention also relates to a novel preparation method of these ligands comprising cyclotrimerization of ethynylestradiol with the appropriate diyne in an organic solvent. Further, the invention relates to pharmaceuticals comprising the novel compounds according to the invention.

18 Claims, 9 Drawing Sheets

(II)

OTHER PUBLICATIONS

Lubahn, D.B. et al. "Alteration of reproductive function but not prenatal sexual development after insertional disruption of the mouse estrogen receptor gene." Proc Natl Acad Sci U S A, 90, 11162-6 (1993).

Hewitt, S.C. & Korach, K.S. "Oestrogen receptor knockout mice: Roles for oestrogen receptors alpha and beta in reproductive tissues." Reproduction, 125, 143-9 (2003).

Kuiper, G.G., Enmark, E., Pelto-Huikko, M., Nilsson, S. & Gustafsson, J.A. "Cloning of a novel receptor expressed in rat prostate and ovary." Proc Natl Acad Sci U S A, 93, 5925-30 (1996).

Gustafsson, J.A. "Estrogen receptor beta—a new dimension in estrogen mechanism of action." J Endocrinol, 163, 379-83 (1999).

Ogawa, S. et al. "The complete primary structure of human estrogen receptor beta (hER beta) and its heterodimerization with ER alpha in vivo and in vitro." Biochem Biophys Res Commun, 243, 122-6 (1998).

Meyers, M.J. et al. "Estrogen receptor-beta potency-selective ligands: structure-activity relationship studies of diarylpropionitriles and their acetylene and polar analogues." J Med Chem, 44, 4230-51 (2001).

Malamas, M.S. et al. "Design and synthesis of aryl diphenolic azoles as potent and selective estrogen receptor-beta ligands." J Med Chem, 47, 5021-40 (2004).

Mewshaw, R.E. et al. "ERbeta ligands. 3. Exploiting two binding orientations of the 2-phenylnaphthalene scaffold to achieve ERbeta selectivity." J Med Chem, 48, 3953-79 (2005).

Hillisch, A. et al. "Dissecting physiological roles of estrogen receptor alpha and beta with potent selective ligands from structure-based design." Mol Endocrinol, 18, 1599-609 (2004).

Couse, J.F. & Korach, K.S. "Estrogen receptor null mice: What have we learned and where will they lead us?" Endocr Rev, 20, 358-417 (1999).

Gustafsson, J.A. "What pharmacologists can learn from recent advances in estrogen signalling." Trends Pharmacol Sci, 24, 479-85 (2003).

Harris, H.A. "Estrogen receptor-beta: Recent lessons from in vivo studies." Mol Endocrinol, 21, 113 (2007).

Koehler, K.F., Helguero, L.A., Haldosen, L.A., Warner, M. &Gustafsson, J.A. "Reflections on the discovery and significance of estrogen receptor beta." Endocr Rev, 26, 465-78 (2005).

Palmieri, C. et al. "Estrogen receptor beta in breast cancer." Endocr Relat Cancer, 9, 1-13 (2002).

Mann, S. et al. "Estrogen receptor beta expression in invasive breast cancer." Hum Pathol, 32, 113-8 (2001).

Omoto, Y. et al. "Clinical value of the wild-type estrogen receptor beta expression in breast cancer." Cancer Lett, 163, 207-12 (2001).

Weihua, Z. et al. "A role for estrogen receptor beta in the regulation of growth of the ventral prostate." Proc Natl Acad Sci U S A, 98, 6330-5 (2001).

Imamov, O. et al. "Estrogenreceptor beta regulates epithelial cellular differentiation in the mouse ventral prostate." Proc Natl Acad Sci U S A, 101, 9375-80 (2004).

Neubauer, B.L. et al. "The selective estrogen receptor modulator trioxifene (LY133314) inhibits metastasis and extends survival in the PAIII rat prostatic carcinoma model." Cancer Res, 63, 6056-62 (2003).

Pearce, S.T. & Jordan, V.C. "The biological role of estrogen receptors alpha and beta in cancer." Crit Rev Oncol Hematol, 50, 3-22 (2004).

Korte, T. et al. "Female mice lacking estrogen receptor beta display prolonged ventricular repolarization and reduced ventricular automaticity after myocardial infarction." Circulation, 111, 2282-90 (2005).

Pelzer, T. et al. "Increased mortality and aggravation of heart failure in estrogen receptor-beta knockout mice after myocardial infarction." Circulation, 111, 1492-8 (2005).

Zhu, Y. et al. "Abnormal vascular function and hypertension in mice deficient in estrogen receptor beta." Science, 295, 505-8 (2002).

Skavdahl, M. et al. "Estrogen receptor-beta mediates male-female differences in the development of pressure overload hypertrophy." Am J Physiol Heart Cir Physiol, 288, H469-76 (2005).

Shughrue, P.H. Lane, M.V. & Merchenthaler, I. "Comparative distribution of estrogen receptor-alpha and -beta mRNA in the rat central nervous system." J Comp Neurol, 388, 507-25 (1997).

Gundlah, C. et al. "Estrogen receptor-beta regulates tryptophan hydroxylase-1 expression in the murine midbrain raphe." Biol Psychiatry, 57, 938-42 (2005).

Walf, A.A. Rhodes, M.E. & Frye, C.A. "Antidepressant effects of ERbeta-selective estrogen receptor modulators in the forced swim test." Pharmacol Biochem Behav, 78, 523-9 (2004).

Shively, C.A., Mirkes, S.J., Lu, N.Z., Henderson, J.A. & Bethea, C.L. "Soy and social stress affect serotonin neurotransmission in primates." Pharmacogenomics J, 3, 114-21 (2003).

Rocha, B.A., Fleischer, R., Schaeffer, J.M., Rohrer, S.P. & Hickey, G.J. "17 Beta-estradiol-induced antidepressant-like effect in the forced swim test is absent in estrogen receptor-beta knockout (BERKO) mice."Psychopharmacology (Berl), 179, 637-43 (2005).

Krezel, W., Dupont, S., Krust, A., Chambon, P. & Chapman, P.F. "Increased anxiety and synaptic plasticity in estrogen receptor beta -deficient mice." Proc Natl Acad Sci U S A, 98, 12278-82 (2001).

Imwalle, D.B., Gustafsson, J.A. & Rissman, E.F. "Lack of functional estrogen receptor beta influences anxiety behavior and serotonin content in female mice." Physiol behav, 84, 157-63 (2005).

Walf, A.A. & Frye, C.A. "ERbeta-selective estrogen receptor modulators produce antianxiety behavior when administered systemically to ovariectomized rats." Neuropsychopharmacology, 30, 1598-609 (2005).

Lund, T.D., Rovis, T., Chung, W.C. & Handa, R.J. "Novel actions of estrogen receptor-beta on anxiety-related behaviors." Endocrinology, 146, 797-807 (2005).

Day, M., Sung, A., Logue, S., Howlby, M. & Arias, R. "Beta estrogen receptor knockout (BERKO) mice present attenuated hippocampal CA1 long-term potentiation and related memory deficits in contextual fear conditioning."Behav Brain Res, 164, 128-31 (2005).

Wang, L., Andersson, S., Warner, M. & Gustafsson, J.A. "Morphological abnormalities in the brains of estrogen receptor beta knockout mice." Proc Natl Acad Sci U S A, 98, 2792-6 (2001).

Wang, L., Andersson, S., Warner, M. & Gustafsson, J.A. "Estrogen receptor (ER)beta knockout mice reveal a role for ERbeta in migration of cortical neurons in the developing brain." Proc Natl Acad Sci U S A, 100, 703-8 (2003).

Taurog, J.D. et al. "Inflammatory disease in HLA-B27 transgenic rats." Immunol Rev 169, 209-23 (1999).

Harris, H.A. et al. "Evaluation of an estrogen receptor-beta agonist in animal models of human disease." Endocrinology, 144, 4241-9 (2003).

Chadwick, C.C. et al. "Identification of pathway-selective estrogen receptor ligands that inhibit NF-kappaB transcriptional activity." Proc Natl Acad Sci U S A, 102, 2543-8 (2005).

Cristofaro, P.A. et al. "WAY-202196, a selective estrogen receptor-beta agonist, protects against death in experimental septic shock." Crit Care Med, 34, 2188-93 (206).

Harris, H.A., Bruner-Tran, K.L., Zhang, X., Osteen, K.G. & Lyttle, C.R. "A selective estrogen receptor-beta agonist causes lesion regression in an experimentally induced model of endometriosis." Hum Reprod, 20, 936-41 (2005).

Cvoro, A. et al. "Selective estrogen receptor-beta agonists repress transcription of proinflammatory genes." J Immunol, 180, 630-6 (2008).

Follettie, M.T., et al. "Organ messenger ribonucleic acid and plasma proteome changes in the adjuvant-induced arthritis model: Responses to disease induction and therapy with the estrogen receptor-beta selective agonist ERB-041." Endocrinology, 147, 714-23 (2006).

Shim, G.J. et al. "Disruption of the estrogen receptor beta gene in mice causes myeloproliferative disease resembling chronic myeloid leukemia with lymphoid blast crisis." Proc Natl Acad Sci U S A, 100, 6694-9 (2003).

Imamov, O., Shim, G.J., Warner, M. & Gustafsson, J.A. "Estrogen receptor beta in health and disease." Biol Reprod, 73, 866-71 (2005).

Witte, D., Chirala, M., Younes, a., Li, Y. & Younes, M. "Estrogen receptor beta is expressed in human colorectal adenocarcinoma." Hum Pathol, 32, 940-4 (2001).

Foley, E.F., Jazaeri, A.A., Shupnik, M.A., Hazaeri, O. & Rice, L.W. "Selective loss of estrogen receptor beta in malignant human colon." Cancer Res, 60, 245-8 (2000).

Hulley, S. et al. "Noncardiovascular disease outcomes during 6.8 years of hormone therapy: Heart and Estrogen/progestin Replacement Study follow-up (HERS II)." JAMA, 288, 58-66 (2002).

LIGANDS OF ESTROGEN RECEPTORS α AND β, METHOD OF THEIR PREPARATION, AND PHARMACEUTICALS COMPRISING THEM

BACKGROUND OF THE INVENTION

Field of the Invention

The invention relates to novel ligands of estrogen receptors α and β, to novel process of their synthesis, and to their use in vitro and in vivo. Ligands of the estrogen receptor α and β according to the invention may be the active component of pharmaceuticals, e.g. pharmaceuticals useful for the hormone replacement therapy or for the treatment of tumor or inflammatory diseases.

Steroid Receptors and the Mechanism of their Activation

The estrogen receptor α (ERα) and the estrogen receptor β (ERβ) are together with the other members of the steroid receptor family transcriptional factors occurring inside the cell and binding the relevant steroid hormones. The steroid hormones like estrogens, androgens, glucocorticoids, mineralocorticoids and progesterone are hydrophobic low molecular weight compounds freely diffusing across the cell membrane into the cell. The unliganded steroid hormone receptor is a part of the cytoplasmic multiprotein complex which prevents the receptor from entering the cell nucleus. The binding of the ligand to the ligand binding domain of the steroid receptor results in the conformational change of the receptor and dissociation of the multiprotein complex. The complex of the steroid receptor with the ligand is subsequently transported to the nucleus where it dimerizes, binds to the specific sequence in promoters of the target genes (so-called HRE, hormone response element), creates complex with appropriate transcription coactivators/corepressors, and modulates the transcription of target genes.

Biological Properties of Estrogen Receptors α and β

The estrogens like the other steroid hormones provoke a wide range of biological responses. Since 1960, it has been believed that the estrogen activity is mediated by a receptor for estrogen receptor. The gene coding for this receptor was cloned in 1986[1, 2] and shortly after that, the ER knockout mouse was prepared[3]. As expected, the loss of the estrogen receptor resulted in a number of serious impairments at the function level in many organs[4]. This phenotype was serious but fully in accordance with the known function of estrogen in a mammal body. In such a situation, the discovery of the gene for the second estrogen receptor—estrogen receptor β—in 1996 was highly surprising[5] and this observation suggested that the broad spectrum of estrogen effects until then attributed to the activity of one single estrogen receptor is in fact mediated by two different receptors with only partially overlapping functions.

Ligands

In the beginning, the research of the ERβ function was predominantly focused on the ERβ expression distribution in different tissues and the binding specificity of ERβ.

It was found that 17β-estradiol is the most potent endogenous ligand and that it binds with similar affinity to both receptors[6]. The ligand-binding domains of both receptors share 56% identity on the amino acid level[7]. However, the homology of binding pockets is significantly higher and the sequence differs only in two amino acids. Nevertheless, these amino acid substitutions create space for the synthesis of ligands with different affinity for individual receptors. Several compounds with different selectivity for ERβ have been indeed prepared recently, the most significant examples thereof being DPN[8], ERB-041[9], WAY-202196[10], WAY-200070[9], and 8β-VE2[11]. These compounds are not structurally similar and therefore they cause different conformational changes after binding to the receptor. These changes are then converted into different biological activities of the receptor in the cell. Furthermore, there is no clear relationship between the affinity of the ligand for the receptor and its ability to activate the receptor.

Use of Selective ERβ Ligands

Although ERβ is expressed in a large number of tissues and cell types, its expression distribution differs substantially from ERα. Today, there is a large amount of experimental data showing that both receptors often have opposite effects in the same tissue[12-14]. For example, in breast epithelial tissue where ERα mediates proliferative effect of estradiol, ERβ, also expressed in this tissue, promotes differentiation and has antiproliferative effect on this tissue[15]. Expression of ERα in breast cancer is considered as an important diagnostic marker essential in the decision-making process for the optimal treatment of patients with breast cancer[6]. Furthermore, higher expression of ERβ is associated with good prognosis for the patient. As an example one study reports that the expression of ERβ is associated with better survival of patients administrated with tamoxifen[17] Moreover, the expression of this receptor has been observed in tumors of patients when disease entered in a symptom-free stage[18]. Taken together, selective ligands for ERβ are compounds exhibiting a broad spectrum of estrogenic effects, but in contrast to estradiol these ligands do not induce proliferation of the breast tumor tissue or they can even suppress its growth.

The other advantage of selective ligands for ERβ consists in the fact that they do not affect the growth of the uterine tissue which is mediated exclusively by ERα[14, 15].

The use of selective ligands for ERβ in the treatment of prostate cancer has been investigated only partially so far. ERβ is the main estrogen receptor expressed in this tissue. The analysis of the ERβ knockout mouse has reported that this receptor has in principle an antiproliferative effect associated with the control of differentiation of various cell type[19, 20]. The simultaneous administration of testosterone and estradiol acts antiproliferatively on prostatic tissue and higher doses of estradiol in combination with testosterone induces apoptosis[14]. Similarly, other works report an antiproliferative effect of ERβ on the prostatic tissue[21]. Therefore, selective ligands for ERβ are promising therapeutic tools for the prostate cancer treatment[15, 22].

In the field of cardiovascular diseases, the analysis of ERβ knockout mice has shown that selective ligands for this receptor might be effective in both the treatment and prevention of the heart stroke[23, 24] and hypertension[25, 26].

ERβ is highly expressed in certain parts of the brain[27]. A very important contribution to the knowledge about the biological function of this receptor was the observation that estradiol increases expression of tryptophan hydroxylase I in serotoninergic neurons in nucleus raphes dorsalis[28], and as a result positively regulates synthesis of serotonin which might cause depressions and anxiety when the concentration drops under certain level in this part of the brain. Studies of the behavior of mice administrated with selective ligands for one of the estrogen receptors report a beneficial effect of the selective ligand for ERβ on both the depression and anxiety[29-35]. Furthermore, it is more and more obvious that these ligands have a great potential in supporting cognitive functions of the brain and especially the memory[36].

Neurons of ERβ knockout mice exhibit a shorter lifespan, and at the age of two years these mice show signs of neurodegeneration, especially in substantia nigra[37, 38]. That implies that selective ligands of ERβ may be used to treat Parkinson's disease or the other neurodegenerative diseases[15].

The rat model of chronic bowel disease represents one of the most promising use of selective ligands of ERβ[39]. These transgenic rats suffer from chronic enteric inflammation accompanied by a strong and persistent diarrhea. The administration of selective ligands of ERβ suppressed both the enteric inflammation and accompanying diarrhea[10, 40]. In addition, the selective ligand of ERβ, WAY-169916, inhibits the transcriptional activity of NF-κB[41], the key transcriptional factor involved in the process of the early and late phase of the inflammatory process, and suggests the possibility of a larger use of selective ligands of ERβ in diseases where the inflammation plays substantial role, i.e., trauma/sepsis[42], endometriosis[43], Alzheimer's disease[44], or rheumatic arthritis[45]. Observations that selective ligands of ERβ suppress the transcription of proinflammatory genes such as TNF-α, IL-6 or CSF2 not only by inhibiting NF-κB but also by direct repression of the transcription by recruitment of specific transcriptional corepressors[41, 44] strongly support the use of these ligands generally in inflammatory diseases.

ERβ knockout mice develop, over the course of time, a myeloproliferative disease resembling human chronic myeloid leukemia with lymphoid blast crisis[46]. Accordingly, ERβ regulates the proliferation of pluripotent haematopoietic progenitors and selective ligands of ERβ are potentially beneficial in the myeloid and lymphoid leukemia treatment[47].

In comparison to ERα, ERβ is strongly expressed in the large intestine. The loss of the receptor expression and/or its relocalization from the nucleus to the cytoplasm occurs in many cases in the course of the malignant transformation[48, 49]. The study of the Women's Health Initiative (WHI) evaluating the use of hormone replacement therapy (administration of estrogen and medroxyprogesterone acetate) in women of 50-79 years resulted in an increased occurrence of breast cancer by 26%[50], but simultaneously in the decrease of colon cancer occurrence by 37%[51]. Since ERα is expressed only in very low level in this tissue, the protective effect is attributed to ERβ[52]. Therefore, the selective ERβ ligands may be potentially used to treat a colon cancer.

The Synthesis of 17-α-Arylestradiols

The synthesis of 17-α-arylestradiols of general formula I was described in the prior art literature:

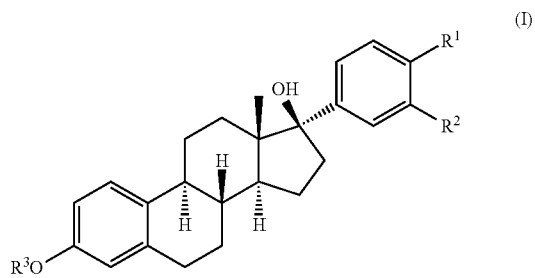

(I)

where $R^1$ is H, $R^2$ is H and $R^3$ is Me;[53, 54] or
where $R^1$ is H, I, $NH_2$, $NMe_2$, N=N—$NEt_2$, N=N—N$(CH_2)_4$, Me, or OMe, $R^2$ is H and $R^3$ is H;[55-57] or
where $R^1$ is H, $R^2$ is I and $R^3$ is H.[5, 58]
wherein Me is methyl and Et is ethyl.

All of these compounds have always been prepared by using the reaction of the relevant aryllithium compounds with estrogen or its derivates. These compounds have been prepared either by simple nucleophile addition of arylmetal compounds on the carbonyl group of estrone or in the presence of $BF_3Et_2O$.[53-58]

None of the compounds mentioned above have shown significant selectivity for one of the estrogen receptors, although in some cases they exhibited a high affinity for both of them.

The British patent application GB 2 361 642 A disclosed agonists of ERβ for the use in cancer treatment. The example of the suitable agonists are genistein or 3βAdiol.

The International patent application WO 00/53620 disclosed derivatives of estradiol that act as inhibitors of steroid sulphatase and can be beneficial in the treatment of some diseases dependent on estrogens.

The International patent application WO 05/048956 disclosed estradiol-related compounds (2.3.4-substituted-E/Z-phenylvinyl-17β-estradiol analogs) which can be beneficial as anti-tumor pharmaceutical agents without reacting substantially with estrogen receptors.

The International patent application WO 05/099704 disclosed the treatment of hypertension, heart dysfunction, or heart stroke by the administration of ERβ agonists.

The International patent application WO 2006/013196 disclosed a method of the synthesis of the 2-substituted derivatives of estrone and estradiol, specifically 2-alkoxyderivatives, mainly methoxyestrone and methoxyestradiol. Some of these compounds can be used as estrogen intermediates, e.g. 2-methoxyestradiol that exhibits very low estrogen activity, but in the same time it has significant biological effects such as the anti-tumor or anti-inflammatory effects.

The U.S. patent application US 2007/0135400 disclosed derivatives of 2-methoxyestradiol, mainly the derivatives modified in the position 2, 3, and 17. The compounds exhibit antimitotic, antiangiogenic and antitumor effects.

The European Patent EP 1 131 336 disclosed specific derivatives of estradiol, 11-β substituted estradiol derivatives exhibiting surprisingly high activity and selectivity for estrogen receptors. The advantageous compounds act as agonists to ERα and antagonists to ERβ. The pharmaceuticals comprising these derivatives are beneficial in the treatment of diseases related to estrogen deficiency.

None of the documents mentioned above disclose compounds that have the structure of novel compounds according to the present invention and exhibit strikingly selective activity at estrogen receptors.

Although many hypotheses about the ER function have been proposed and practically thousands of papers have been published, the precise functions of ERα and ERβ are not clear enough yet. A lot is known about the possibilities of the use of selective ligands in the therapy, and ERβ selective ligands are supposed to be the most interesting. Consequently, there is a continual need for novel ligands exhibiting selective activity. These ligands will find their use as a tool in both biological and pharmaceutical research, as well as in pharmaceutical agents.

SUMMARY OF THE INVENTION

Novel derivatives of estradiol described below in the present application show agonistic activity on estrogen receptors ERα and ERβ, some of them with the strikingly selective activity, namely β selective activity.

The invention teaches novel ligands of the estrogen receptors α and β of general formula II that are useful as active pharmaceutical substances, such as, for example, pharmaceutical compositions that are useful for hormone replacement therapy, as well as for the treatment of tumor and inflammatory diseases. The invention also teaches a novel method of preparation of these ligands comprising cyclotrimerization of ethynylestradiol with the appropriate diyne in an organic solvent. Further, the invention teaches to pharmaceuticals comprising the novel compounds according to the invention.

The invention teaches a compound of the general formula II

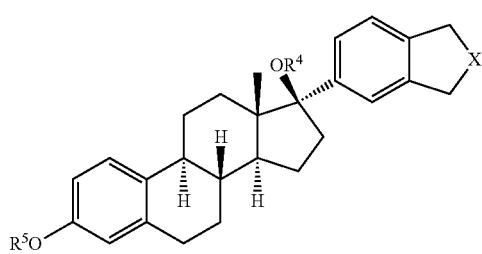

(II)

wherein X is C or heteroatom selected from the group consisting of N, O, S, wherein X optionally carries one or two substituents independently selected from the group consisting of alkyl, aryl, carboxyl, esterified carboxyl, hydrogencarbonyl, alkylcarbonyl and nitrile groups, or X is NTs;

$R^4$ is H or alkyl;

$R^5$ is H, alkyl, aryl, or acyl;

and isomeric forms, salts, and solvates thereof.

The invention further teaches that the compound described above may be selected from the following compounds:

PN202

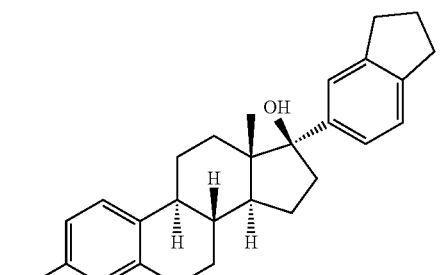

PN207

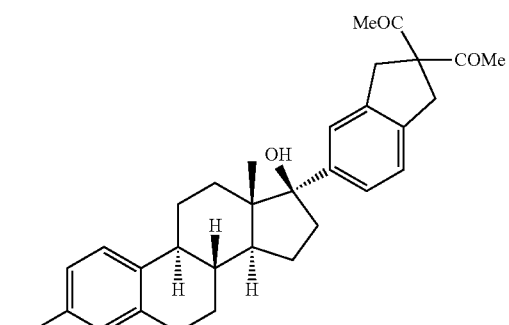

PN214

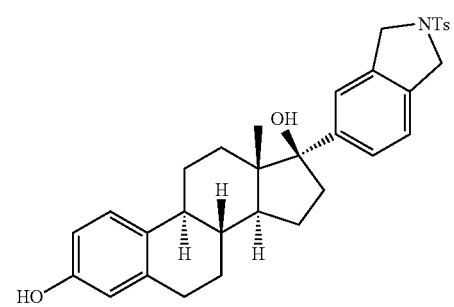

PN228

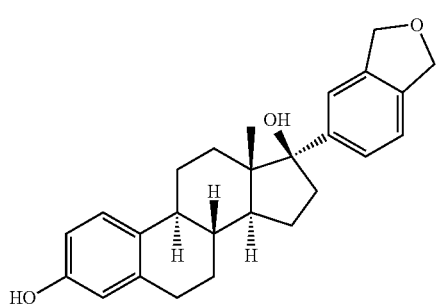

PN229

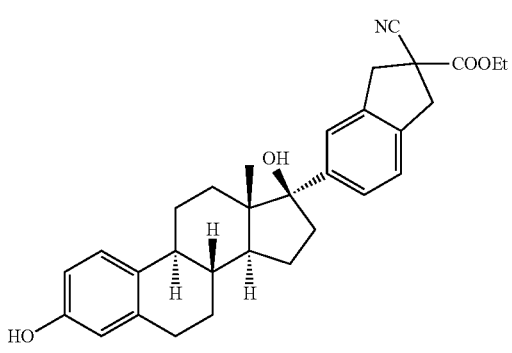

PN232

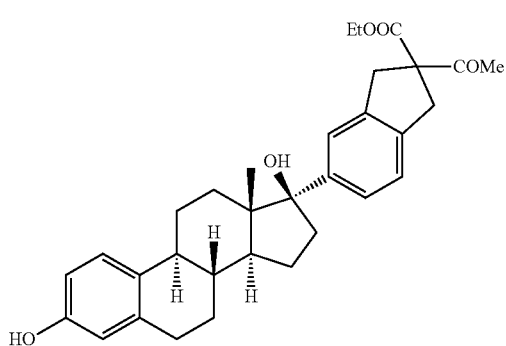

PN233

The invention still further teaches that the compound may be selected from the compounds of formulas PN214, PN229, and PN233 mentioned above.

The invention yet further teaches a method of the preparation of the compound described above, comprising cyclotrimerization of ethynylestradiol in an organic solvent with the diyne of the general formula III

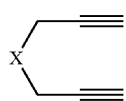
(III)

wherein X is as defined above, under the addition of a catalyst in the form of a transition metal complex, and optionally removing the solvent and purifying the product.

The invention still further teaches the method described above wherein ethynylestradiol is 17α-ethynylestradiol, and/or
the organic solvent is selected from toluene, benzene, THF, dichloromethane, acetonitrile, and mixtures thereof, more preferably from toluene and acetonitrile, most preferably the organic solvent is a mixture of dry toluene and acetonitrile, and/or
the catalyst is selected from the transition metal complexes, preferably from Ru, Rh, Co, Ni complexes, and combinations thereof, more preferably from $Ni(cod)_2/PPh_3$ and $RhCl(PPh_3)_3$, and most preferably the catalyst is $RhCl(PPh_3)_3$.

The invention yet further teaches the method described above wherein the molar ratio of ethynylestradiol to diynes of the formula III is approximately 2:1 to 1:5, more preferably approximately 1:1 to 1:2, most preferably approximately 1:1.2, and/or
the reaction is carried out under stirring, preferably at 15 to 100° C., more preferably at 15 to 60° C., and most preferably at 20° C., and/or
the reaction is carried out for 8 to 72 hours, more preferably for 24 to 48 hours, most preferably until the starting compounds are completely consumed.

The invention still further teaches the compound prepared by any of the methods above.

The invention yet further teaches the compounds described above for use as a medicament.

The invention still further teaches the compounds described above, optionally together with pharmaceutically acceptable excipients.

The invention yet further teaches the use of the compounds described above in the production of a medicament.

DESCRIPTION OF THE DRAWINGS

These and other advantages of the present invention are best understood with reference to the drawings, in which.

Figure 1:
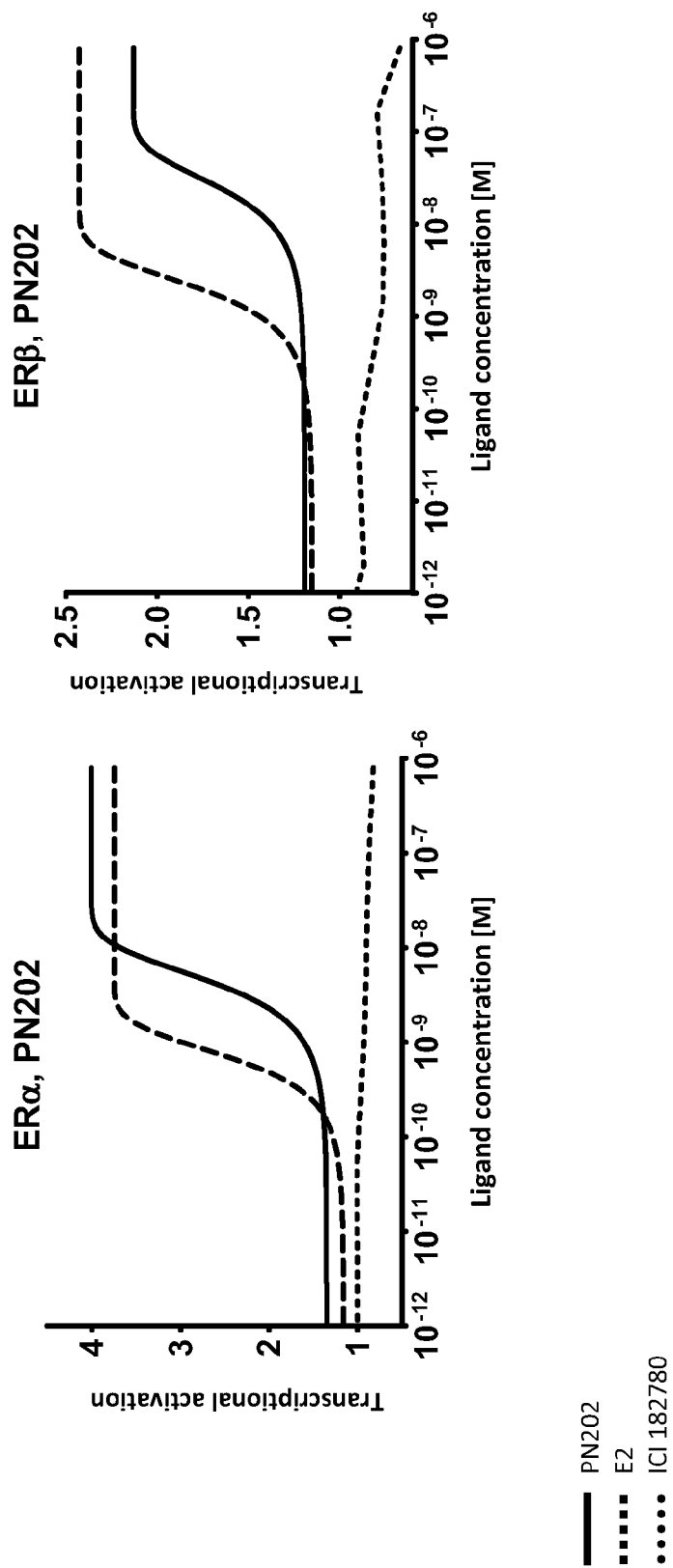
FIG. 1 graphically depicts for the ligand PN202 the relationship between ERα and ERβ transcriptional activity versus ligand concentration.
Figure 2:
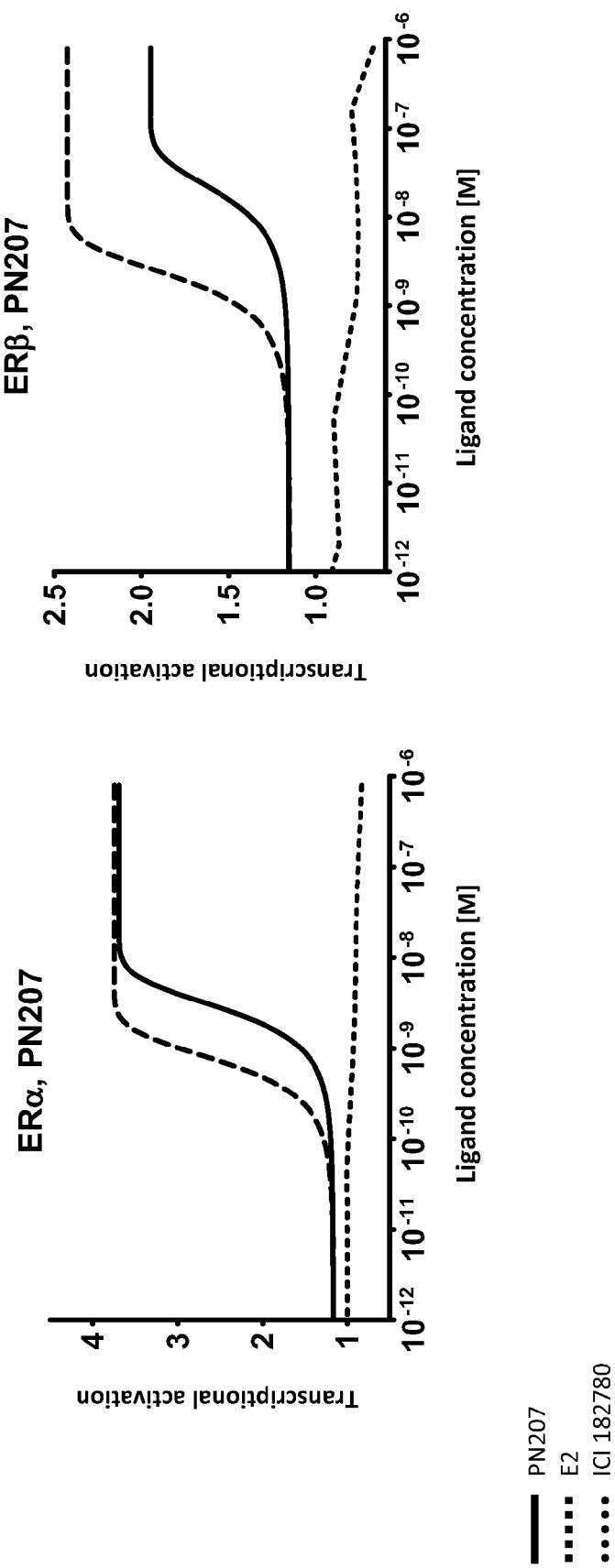
FIG. 2 graphically depicts for the ligand PN207 the relationship between ERα and ERβ transcriptional activity versus ligand concentration.
Figure 3:
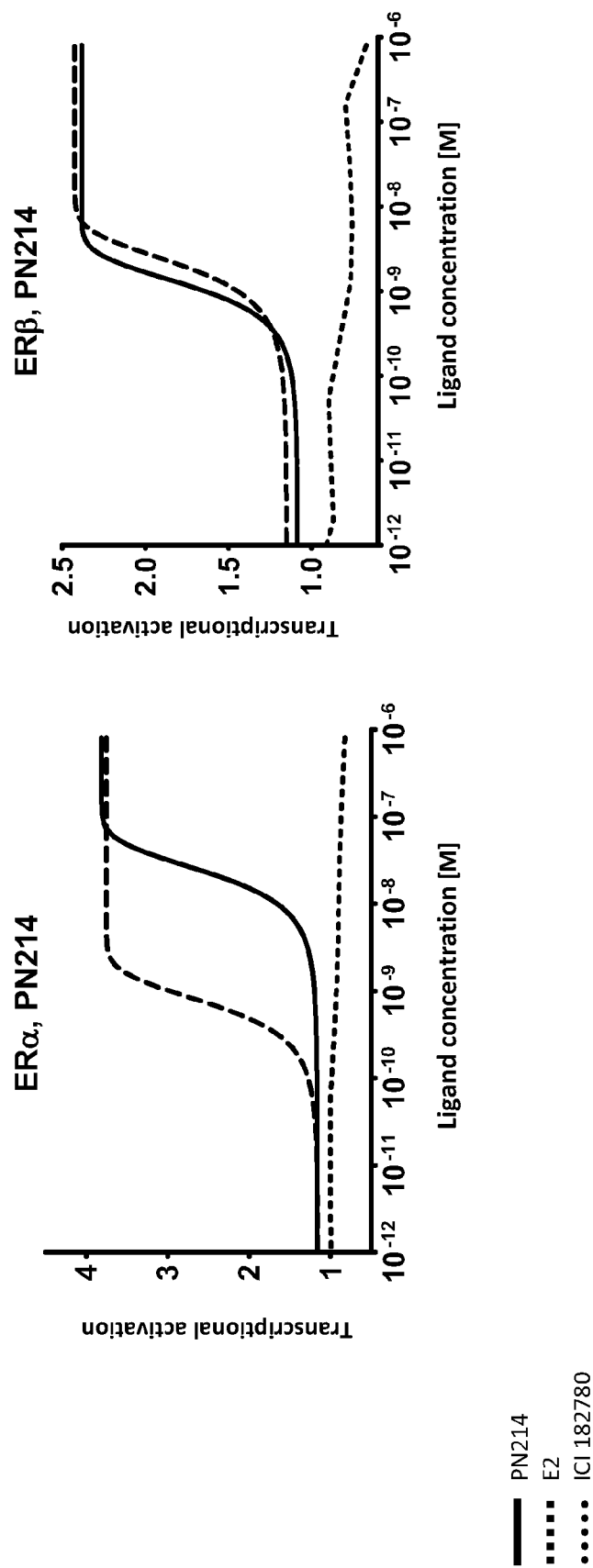
FIG. 3 graphically depicts for the ligand PN214 the relationship between ERα and ERβ transcriptional activity versus ligand concentration.
Figure 4:
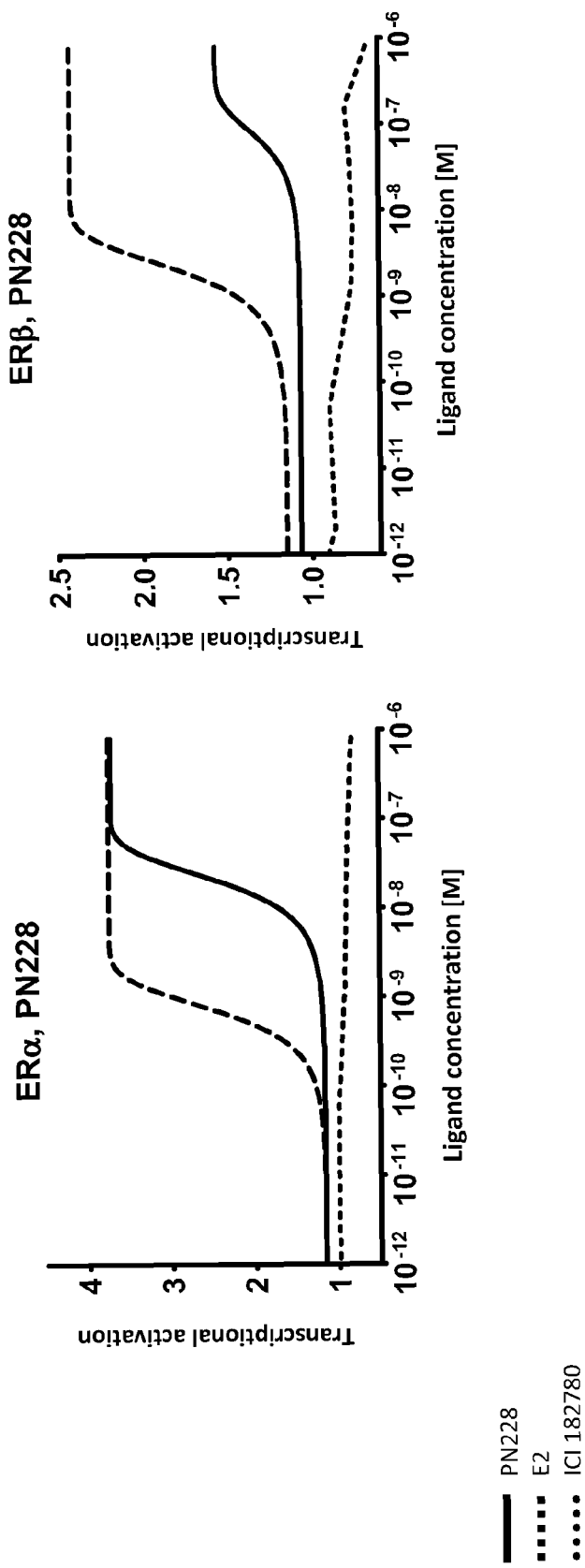
FIG. 4 graphically depicts for the ligand PN228 the relationship between ERα and ERβ transcriptional activity versus ligand concentration.
Figure 5:
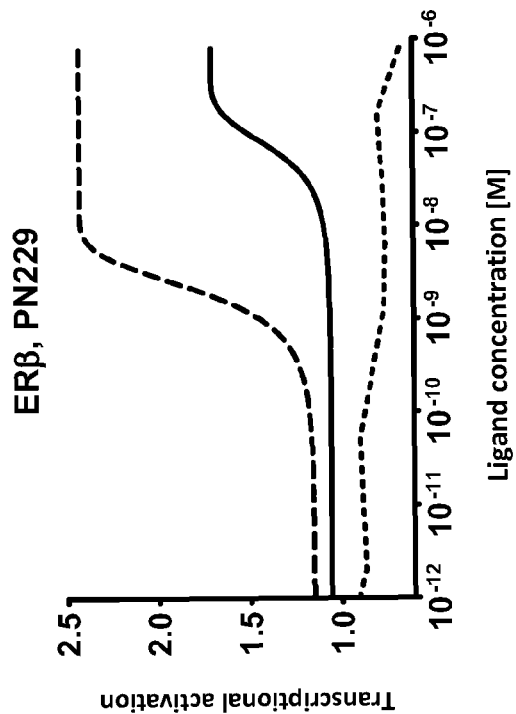
FIG. 5 graphically depicts for the ligand PN229 the relationship between ERα and ERβ transcriptional activity versus ligand concentration.
Figure 5:
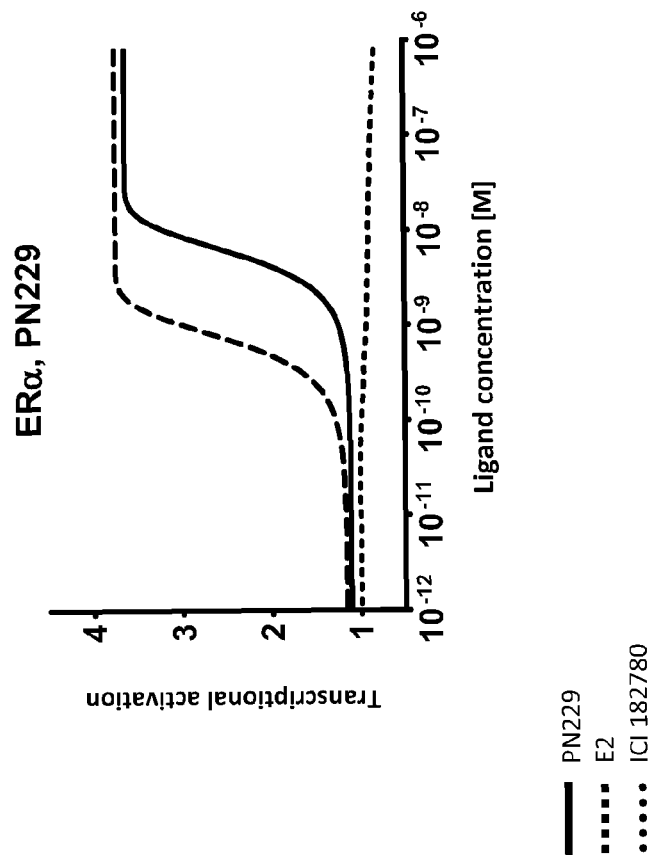
Figure 6:
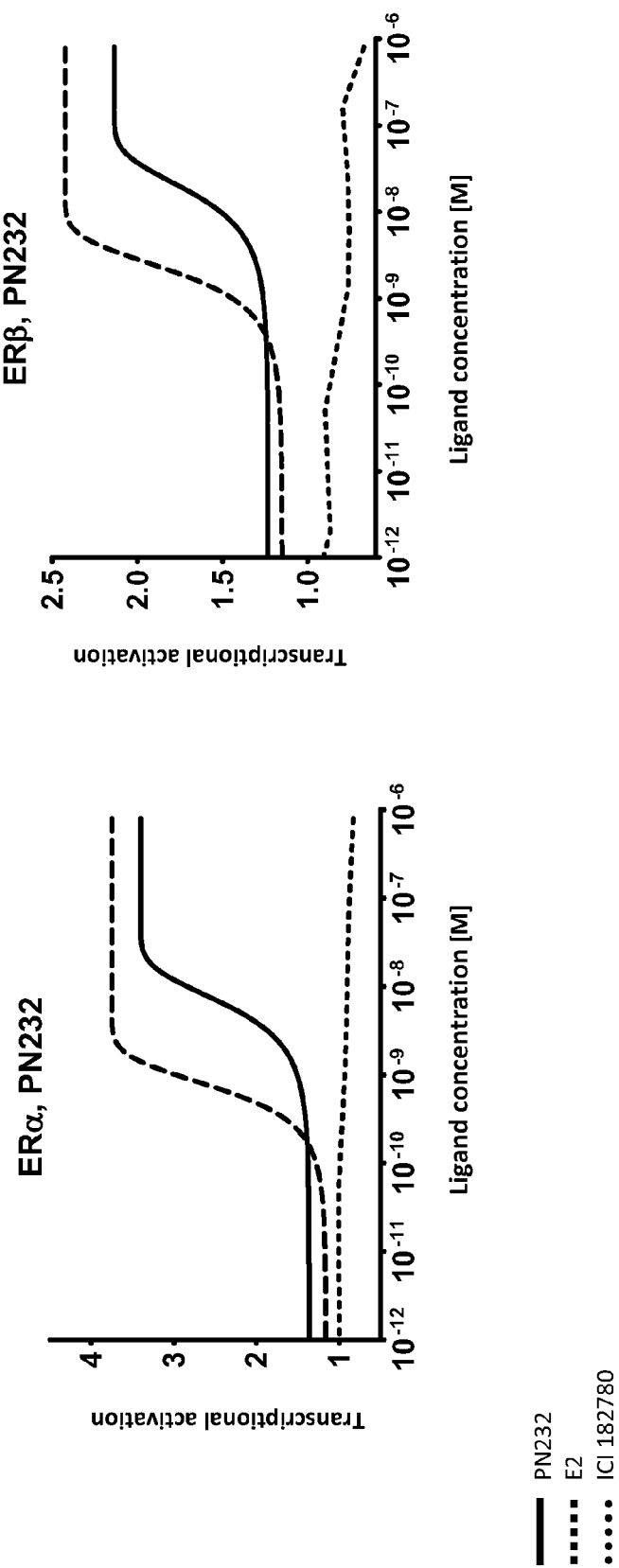
FIG. 6 graphically depicts for the ligand PN232 the relationship between ERα and ERβ transcriptional activity versus ligand concentration.
Figure 7:
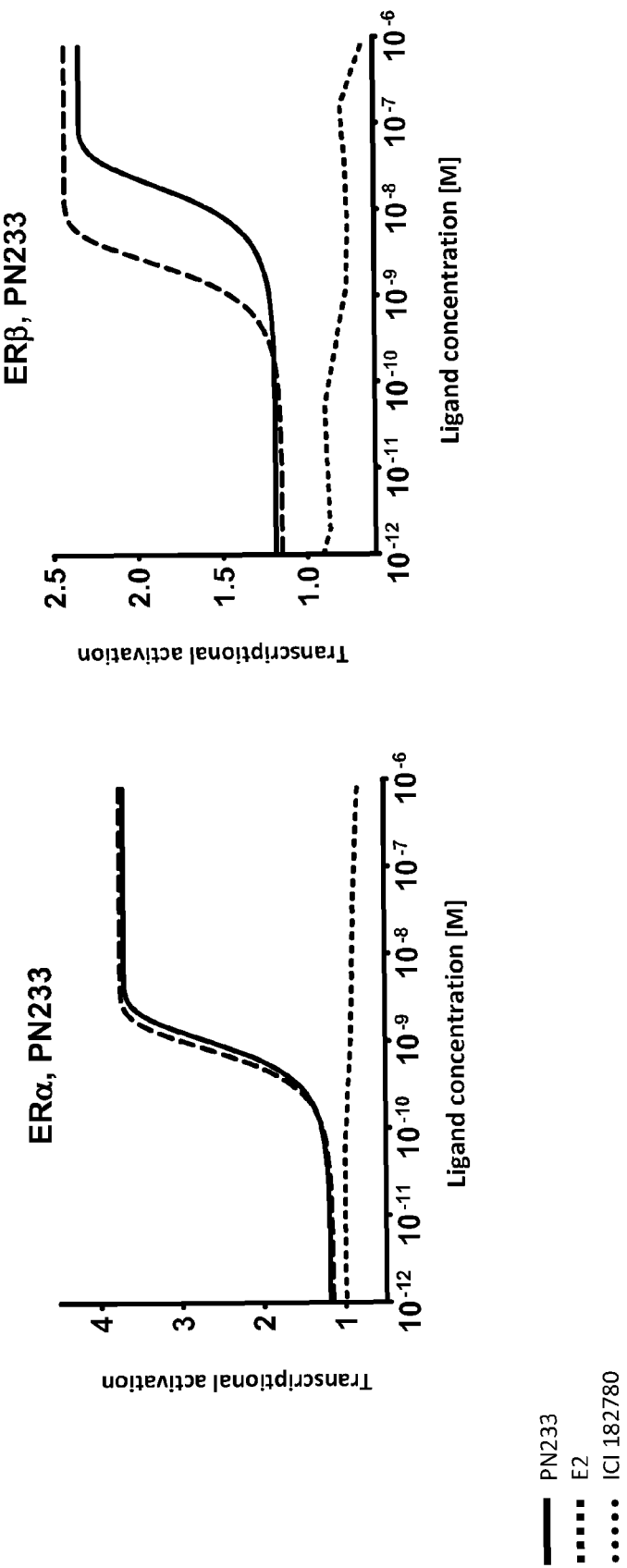
FIG. 7 graphically depicts for the ligand PN233 the relationship between ERα and ERβ transcriptional activity versus ligand concentration.

In these figures, E2 denotes estradiol and ICI 182 780 is 13-methyl-7-[9-(4,4,5,5,5-pentafluorpentylsulfinyl)nonyl]-7,8,9,11,12,13,14,15,16,17-decahydro-6H-cyclopenta[a]-phenanthrene-3,17-diol.

DETAILED DESCRIPTION OF THE EXEMPLARY EMBODIMENTS

Novel Compounds

Novel 17α-indanylestradiols offers new possibilities of modulating the activity of ERα and ERβ. Some of them are selective ligands for ERβ and, in addition, they lack the disadvantages of the existing selective ligands. Novel compounds according to the invention are the compounds having the general formula II

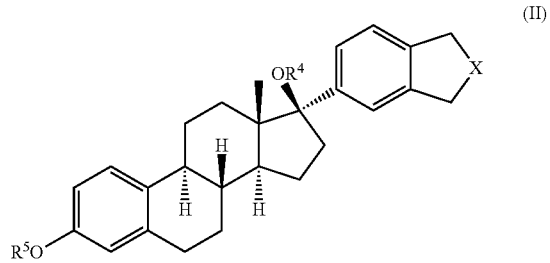
(II)

where
X is C or heteroatom selected from the group consisting of N, O, S, wherein X optionally carries one or two substituents independently selected from the group consisting of alkyl, aryl, carboxyl, esterified carboxyl, hydrogencarbonyl, alkylcarbonyl and nitrile groups, or X is NTs. Preferably, the substituents of X are selected from the group consisting of H, COO-Et, COMe, CN. More preferably, X represents $C(COOEt)_2$, $C(COMe)_2$, C(COOEt)COMe, C(COOEt)CN, CH2, O, NTs, most preferably CH2, NTs, and C(COOEt)CN, wherein Et is ethyl, Me is methyl and NTs is p toluensulphoamido,
$R^4$ is H or alkyl, most preferably H,
$R^5$ is H, alkyl, aryl, or acyl, more preferably H, alkyl, or acyl, most preferably H or methyl.

Alkyl is a hydrocarbon residue formed by removal of one or more hydrogen atoms from the hydrocarbon molecule (hydrocarbon is a molecule with straight or branched carbon skeleton containing only C—C and C—H bonds), and preferably contains 1 to 8 carbon atoms, more preferably 1 to 4 carbon atoms. Typical examples of alkyl groups are, e.g. methyl, ethyl, n-propyl, isopropyl, n-butyl, sec-butyl, tert-butyl etc., the most preferable being methyl and ethyl.

Aryl is a group formed by removal of one or more hydrogens from the arene molecule (arenes are aromatic benzenoid hydrocarbons, comprising benzene and hydrocarbons derived from it either by substitution of one or more hydrogens by hydrocarbon residues, or by fusing other cycles to form polynuclear condensed hydrocarbons, wherein the adjacent rings always share two carbon atoms). According to the present invention, the aryl group preferably contains 6 to 14 carbon atoms. The typical examples of aryl groups are, e.g. phenyl, naphthyl, indenyl, anthracene, fenanthrene, etc., the most preferable being phenyl or naphthyl.

Acyl is an organic residue formed by removal of hydroxyl group from carboxyl of carboxylic acids, preferably of alkylcarboxylic or arylcarboxylic acids, where alkyl and aryl are as defined above. The typical examples of acyl groups are benzoyl, formyl, or acetyl.

The carbonyl group consists of a carbon atom bonded to an oxygen atom by a double bond to form a carbonyl group of formula —C(O)—. In the compound according to the invention, one of its free bonds is connected to X and the other one carries a hydrogen atom (hydrogencarbonyl group) or an alkyl group (alkylcarbonyl group), as defined above.

The carboxyl group consists of a carbonyl group, wherein a hydroxyl group is bonded to the carbon atom to form a carboxyl group of formula —C(O)OH. The esterified carboxyl group is a group of formula —C(O)OR, wherein R is alkyl or aryl, as defined above.

The nitrile group consists of a carbon atom bound to a nitrogen atom by a triple bond.

The preferable compounds according to the present invention are compounds labeled as PN202, PN207, PN214, PN228, PN229, PN232, and PN233, having the formulas shown below:

PN202
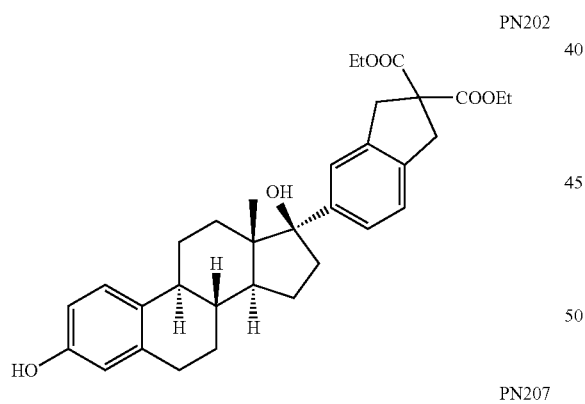

PN207
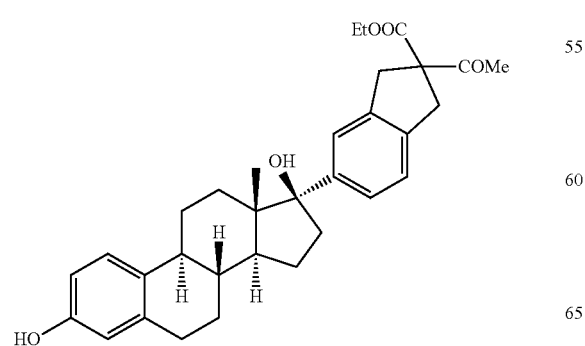

-continued

PN214
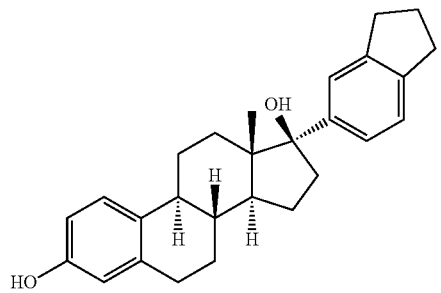

PN228
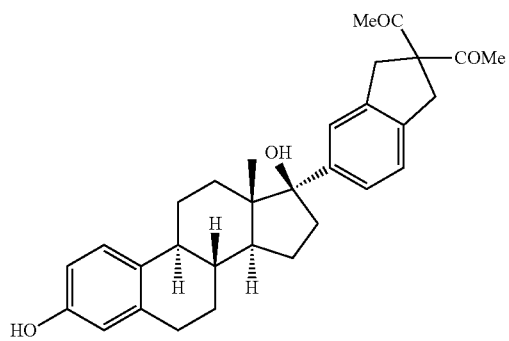

PN229
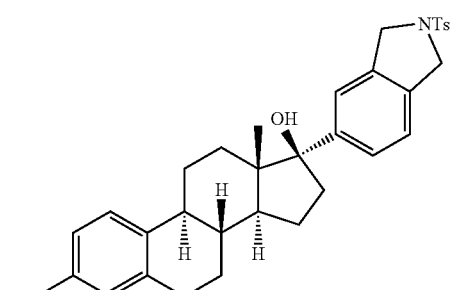

PN232
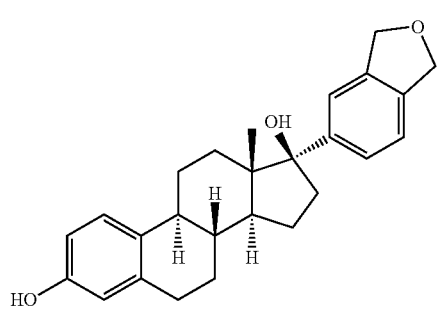

PN233
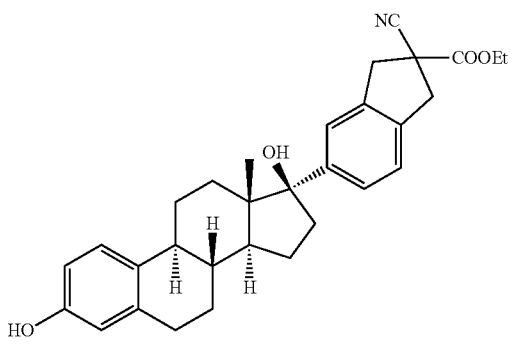

Based on the activity test of compounds described above in reporter assays in COS-7 cell-line (see Example 13), it can be summarized that novel compounds are highly potent ligands of both of the estrogen receptors, and that their potency is comparable to estradiol. This is an important property from the therapeutic point of view, because these compounds are effective in very low concentrations and their administration is not associated with side effects, such as cross-reactivity with other members of the nuclear receptor family, the interference with the metabolism of steroid compounds, or the general toxicity of compounds in the body. The compounds PN202, PN207, PN214, PN229, PN232, and PN233 seem to be preferable ligands, and the compounds PN214 and PN233 seem to be the most preferable ligands.

Moreover, the novel compounds exhibit distinct selectivity to one of the estrogen receptors. Here, the compounds PN229 and PN233 seem to be the preferable selective ligands for ERα and the compound PN214 seem to be the preferable selective ligands for ERβ.

The compound PN214 seems to be the most preferable selective ligand for ERβ, the selectivity of this ligand being comparable to the best known selective ligands for this receptor.

Proliferation studies carried out with the same compounds (see Example 14 below) support the previous finding that the compound PN214 is highly selective ligand for ERβ.

The compounds of general formula II defined above have not been disclosed in the literature so far. Consequently, none of these compounds have been tested for affinity to ERα or ERβ.

The present invention includes also compounds of formula II described above in all isomeric forms thereof, as well as salts and solvates thereof. Methods suitable for the synthesis of enantiomer mixtures as well as the isolated enantiomers of compounds according to the present invention are known to the persons skilled in the art[53-58], and therefore such methods may be used to prepare them in a routine manner. The invention includes also the products of the compounds according to the invention, i.e. compounds that are in vivo metabolized to the active compound after being administered. Within the present description, the term "compound(s) according to the invention" is used for all these compounds in all these forms.

The present invention includes also each of the individual compounds of the formula II described above individually.

The Novel Method of the Preparation of Compounds According to the Invention

The compounds according to the invention defined above were prepared by the novel method which consists of the cyclotrimerization of the ethynylestradiol derivatives with appropriate diynes under the catalysis by transition metal complexes in organic solvents.

Accordingly, the subject-matter of the present invention is also a method of the preparation of the compound of general formula II defined above, comprising cyclotrimerization of ethynylestradiol in an organic solvent, with dyine of general formula III

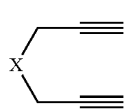
(III)

where X is as defined above for general formula II, under the addition of a catalyst in the form of a transition metal complex. Then, if needed, the solvent is removed by a common method, e.g. by evaporation, and the residue is, if needed, purified by common methods, e.g. by chromatography on silica gel.

17α-ethynylestradiol is preferably used as ethynylestradiol.

Diynes used in the method according to the invention are preferably diynes of general formula III, where X is as defined above for general formula II. The most preferable diynes of general formula III are chosen from the following compounds:

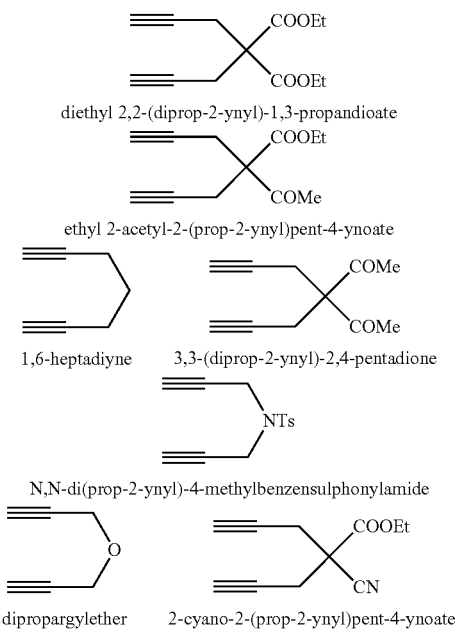

diethyl 2,2-(diprop-2-ynyl)-1,3-propandioate ethyl 2-acetyl-2-(prop-2-ynyl)pent-4-ynoate 1,6-heptadiyne    3,3-(diprop-2-ynyl)-2,4-pentadione N,N-di(prop-2-ynyl)-4-methylbenzensulphonylamide dipropargylether    2-cyano-2-(prop-2-ynyl)pent-4-ynoate The organic solvent used in the method according to the invention can be any appropriate organic solvent known to the person skilled in the art, e.g. chosen from toluene, benzene, THF, dichloromethane, acetonitrile, etc., and mixtures thereof, more preferably from toluene and acetonitrile, the most preferable solvent being a mixture of dry toluene and acetonitrile.

The catalyst used in the method according to the invention is chosen from transition metal, e.g. Ru, Rh, Co, Ni, complexes, and combinations thereof, more preferably from $Ni(cod)_2/PPh_3$ and $RhCl(PPh_3)_3$, the most preferable being $RhCl(PPh_3)_3$ [$Ni(cod)_2/PPh_3$ is bis(hapto-4-cycloocta-1,5-diene)nickel/tri-phenylphosphane, $RhCl(PPh_3)_3$ is tris(triphenylphosphane)-rhodium chloride complex.].

The reaction is preferably carried out under stirring, preferably at the temperature 15 to 100° C., more preferably at the temperature 15 to 60° C., most preferably at 20° C., preferably for 8 to 72 hours, more preferably for 24 to 48 hours, most preferably until the starting compounds are completely consumed, which can be easily verified by, e.g., thin-layer chromatography (TLC).

The molar ratio of the ethynylestradiol to diynes III is preferably approximately 2:1 to 1:5, more preferably approximately 1:1 to 1:2, and most preferably approximately 1:1.2.

In a preferred embodiment of the method according to the invention, $RhCl(PPh_3)_3$ (0.05 mmol, 46 mg) and the diyne of general formula III (0.6 mmol) are added to a solution of 17α-ethynylestradiol (0.5 mmol, 150 mg) in the mixture of dry toluene (6 ml) and acetonitrile (1 ml). The reaction mixture is stirred at 20° C. for 48 hours until the starting compounds are completely consumed (as controlled by TLC). The solvents are then evaporated and the residue is treated by chromatography on silica gel.

It will be understood by persons skilled in the art that the described method can be modified (the modification of some of parameters, e.g. temperature or solvent or mixture of solvents), as well as other routine steps (e.g. purification) possibly being added thereto, which doesn't depart from the principle of the method according to the invention. These optional modifications and additions fall within the scope of the present invention as well.

Pharmaceutical Compositions Comprising the Compounds According to the Invention

Today, the most commonly used new synthetic ligands of estrogen receptors don't have steroid character and their use as medicaments in medicine is accompanied by a number of problems such as genotoxicity, low stability of ligands in the patient body, unknown or potentially problematic metabolism of these compounds and, last but not least, the transport problems of these compounds to the target place in the body. Since the novel ligands of estrogen receptors according to the present invention are estradiol derivatives, both the pharmacological and the toxicological profiles are expected to be similar to the other steroid hormones.

As mentioned above (see the Background of the Invention), ER ligands have important pharmacological effects. Therefore, the ligands according to the present invention can be used as pharmaceuticals or active components of medicaments. The ligands according to the invention can be active components of pharmaceutical compositions useful for hormone replacement therapy or for the treatment of diseases that can be treated by ER, especially ERβ, targeting (modulating), e.g. tumor or inflammatory diseases as mentioned above.

The term "treatment" stands for the administration of a medicament for both curative and prophylactic purposes. ER modulating or targeting means that the compound according to the invention can act as agonist/antagonist, partial agonist/antagonist or selective agonist/antagonist of estradiol.

Therefore, the subject-matter of the invention is also a pharmaceutical composition comprising the compound according to the invention as the active component.

The pharmaceuticals (pharmaceutical compositions, medicaments, preparations) according to the invention are intended for the treatment of cancer, e.g. prostate cancer, colorectal cancer, and myeloid and lymphoid leukemia, for the treatment of inflammatory diseases, e.g., bowel inflammatory diseases and other inflammatory diseases, for the treatment of diseases where inflammation plays an important role, such as trauma/sepsis, endometriosis, Alzheimer's disease, or rheumatoid arthritis, further for the treatment of psychiatric and neurological diseases, such as depression, anxiety, memory disorders, and learning process disorders, for the treatment of neurodegenerative diseases such as Parkinson's disease, and for the treatment of cardiovascular diseases, such as myocardial infarction and hypertension. Furthermore, the compounds according to the invention can be used as a specific pharmaceutical agent which provides a number of estrogenic effects, without being uterotrophic and inducing the growth of mammary glands or breast cancer tissue.

The pharmaceutical compositions according to the invention comprise the compound according to the invention in a pharmaceutically effective amount as the active substance. The method for determining the pharmaceutically effective amount is a routine procedure that will be well known to persons skilled in the art.

In the pharmaceutical composition, the compounds according to the invention may also be present in the form of pharmaceutically acceptable salts (non-toxic, physiologically acceptable), of an inorganic or organic nature. Examples of such appropriate salts are hydrochloride or methansulfonate, and the skilled artisan will be capable of preparing the appropriate salts.

The compounds according to the present invention may be present in a pharmaceutical composition according to the invention in the form of a prodrug.

The pharmaceutical compositions according to the invention are intended mainly for the treatment of humans, but can be also used to treat other mammals such as livestock or domestic animals.

The pharmaceutical compositions comprising compounds according to the invention, isomers or salts thereof, can be formulated for systemic administration, e.g., enteral administration, such as oral administration, e.g., in the form of tablets or capsules, for rectal administration, e.g., in the form of suppositories, and for nasal administration or for inhalation, e.g., in the form of spray or drops. Furthermore, they can be formulated for topical or local administrations, e.g., in the form of buccal tablets or ointments or patches or in the form of more complex transdermal systems. The compositions according to the invention can be formulated for parenteral administration, such as via injection (i.v., i.m., s.c.), infusion, or implanted reservoir system. It will be apparent to a person skilled in the art that this specification is not exhaustive, and other appropriated methods of administration will be apparent to a skilled artisan.

The active substance is typically present in the pharmaceutical composition together with excipients, such as fillers, disintegrators, diluents, solvents, binders, emulsifying agents, buffers, stabilizing agents, preservatives, and coloring agents. The excipients and their use in the formulations are well known to those skilled in the art.

The compound according to the invention can be comprised in a pharmaceutical composition in combination with other active substances, for example with a compound exhibiting a synergistic effect.

The determination of the dosage of the active substance in one unit dosage form, e.g., in a capsule, or e.g., in a suitable concentration of injection or infusion solution, is also a routine procedure that will be apparent to a skilled artisan.

The skills in the art mentioned above referring to the pharmacological compositions, dosage forms, excipients, etc., are summarized in the specialized literature[59-60] readily available to skilled artisans, e.g. in the Czech Pharmacopoeia (ČL, 2005, 2007), in the European Pharmacopoeia (Ph. Eur.), and/or in the U.S. Pharmacopoeia (USP).

The following examples serve to better illustrate, but not limit in any manner, some of the preferred embodiments of the present invention described above and defined in the claims.

EXAMPLES

The General Method for the Synthesis of the Compounds According to the Invention The novel compounds according to the invention were prepared by the novel methods according to the invention, i.e. by cyclotrimerisation as described above. In particular, the preferable method was used: RhCl(PPh$_3$)$_3$ (0.05 mmol, 46 mg) and appropriate diyne of general formula III (0.6 mmol) were added to the solution of 17α-ethynylestradiol (0.5 mmol, 150 mg) in the mixture of dry toluene (6 ml) and acetonitrile (1 ml). The reaction mixture was stirred at 20° C. for 48 hours or until the starting compounds were completely consumed (as controlled by TLC). The solvents were then evaporated and the residue was treated by chromatography on silica gel. This method produced a colorless compound which was further characterized by 1H and 13C NMR spectroscopy, infra-red spectroscopy and mass spectroscopy.

Using this general method and by the use of starting compounds described above following advantageous compounds were prepared:

Example 1

PN202: 17α[2,2-Bis(ethoxycarbonyl)-1,3-dihydro-2H-inden-5-yl]-estradiol

17α-Ethynylestradiol (0.25 mmol, 74 mg), diethyl 2,2-(diprop-2-ynyl)-1,3-propandioate (0.3 mmol, 70.8 mg), RhCl(PPh$_3$)$_3$ (0.025 mmol, 23 mg). Column chromatography on silica gel (2/1 hexan/EtOAc) yielded 75 mg (56%) of a colorless compound.

M.p. 164° C.; [α]D=+35° (c 0.022 g/ml, acetone); $^1$H NMR (400 MHz, C6D6) δ 0.71-0.79 (m, 1H), 0.87 (t, J=6.8 Hz, 3H), 0.88 (t, J=6.8 Hz, 3H), 1.06 (s, 3H), 1.03-1.12 (m, 1H), 1.29-1.42 (m, 4H), 1.61-1.75 (m, 4H), 1.88-2.00 (m, 2H), 2.18-2.23 (m, 1H), 2.58-2.70 (m, 2H), 3.73-3.85 (m, 4H), 3.91 (q, J=6.8 Hz, 2H), 3.92 (q, J=6.8 Hz, 2H), 5.14 (s, 1H), 6.47 (d, J=2.8 Hz, 1H), 6.57 (dd, J=8, 2.8 Hz, 1H), 6.94 (d, J=8 Hz, 1H), 7.04 (d, J=8 Hz, 1H), 7.164 (s, 1H) signal overlapped, 7.37 (s, 1H); $^{13}$C NMR (100 MHz, C6D6) δ 14.60 (2×), 15.74, 25.05, 27.33, 28.46, 30.62, 34.67, 39.63, 40.46, 41.37, 41.76, 44.20, 47.83, 49.15, 61.66, 62.35 (2×), 86.64, 113.73, 116.23, 123.90, 124.49, 127.40, 129.23, 133.05, 138.56, 139.50, 140.19, 146.60, 155.06, 172.47 (2×); IR (ATR ZnSe) ν 3398, 2958, 2927, 2870, 1727, 1711, 1610, 1502, 1442, 1283, 1249, 1185, 1068, 1049, 1008 cm$^{-1}$; MS (EI) 532 (8), 514 (72), 499 (17), 425 (17), 314 (12), 213 (56), 149 (77); HRMS (EI) calculated for C$_{33}$H$_{40}$O$_6$ 532.282489. Found 532.283226.

Example 2

PN207: 17α-[2-Acetyl-2-(ethoxycarbonyl)-1,3-dihydro-2H-inden-5-yl]-estradiol

17α-Ethynylestradiol (0.5 mmol, 150 mg), ethyl 2-acetyl-2-(prop-2-ynyl)pent-4-ynoate (0.6 mmol, 106 mg), RhCl(PPh3)3 (0.05 mmol, 46 mg). Column chromatography on silica gel (2/1 hexan/EtOAc) yielded 103 mg (41%) of a diastereoisomer mixture as colorless compounds.

M.p. 113° C.; [α]D=+28.7° (c 0.023 g/ml, acetone); $^1$H NMR (400 MHz, C6D6) δ 0.58-0.64 (m, 2×1H), 0.96 (s, 3H), 1.05 (s, 3H), 1.22 (t, J=7.2 Hz, 3H), 1.23 (t, J=7.2 Hz, 3H), 1.28-1.39 (m, 2×5H), 1.52-1.74 (m, 2×2H), 1.84-1.93 (m, 2×2H), 1.99-2.07 (m, 2×2H), 2.20 (s, 3H), 2.21 (s, 3H), 2.31-2.39 (m, 2×1H), 2.70-2.80 (m, 2×2H), 3.41-3.51 (m, 2×4H), 4.18 (q, J=7.2 Hz, 2H), 4.19 (q, J=7.2 Hz, 2H), 4.85 (bs, 2×1H), 6.43 (d, J=2.4 Hz, 2×1H), 6.47 (dd, J=8.4, 2.4 Hz, 2×1H), 6.92 (d, J=8 Hz, 2×1H), 7.12 (d, J=8 Hz, 2×1H), 7.16-7.17 (m, 2×1H), 7.25 (s, 2×1H); $^{13}$C NMR (100 MHz, CD3OD) δ 14.31, 14.50, 15.57, 15.72, 25.07, 25.08, 26.31, 26.38, 27.36, 27.54, 28.47, 28.72, 30.62, 30.70, 34.71, 34.90, 38.91, 39.65, 39.69, 40.05, 40.12, 40.49 (2×), 41.15, 44.23, 44.81, 47.85, 47.99, 49.18, signal overlapped, 62.27, 62.90, 68.04, 68.34, 86.55, 86.84, 113.62, 113.69, 115.97, 116.19, 123.76, 123.94, 124.53, 127.11, 127.39, 127.59, 128.24, 129.24, 132.54, 133.06, 138.54, 138.72, 139.37, 139.46, 140.09, 140.10, 146.64, 146.75, 155.00, 155.82, 173.15, 173.87, 202.26, 204.79; IR (ATR ZnSe) ν 3398, 2955, 2923, 2870, 1711, 1692, 1610, 1502, 1442, 1353, 1283, 1242, 1182, 1154, 1078, 1011 cm$^{-1}$; MS (EI) 502 (<1), 314 (10), 213 (16), 149 (40), 43 (100); HRMS (EI) calculated for C$_{32}$H$_{38}$O$_5$ 502.271925. Found 502.269356.

Example 3

PN214: 17α-(1,3-Dihydro-2H-inden-5-yl)-estradiol

17α-Ethynylestradiol (0.25 mmol, 74 mg), 1,6-heptadiyne (0.3 mmol, 35 μl), RhCl(PPh3)3 (0.025 mmol, 23 mg). Column chromatography on silica gel (2/1 hexane/EtOAc) yielded 56 mg (58%) of a colorless compound.

M.p. 226° C.; [α]D=+57.2° (c 0.009 g/ml, acetone); $^1$H NMR (400 MHz, DMSO) δ 0.50-0.53 (m, 1H), 0.96 (s, 3H), 1.13-1.33 (m, 4H), 1.43-1.49 (m, 2H), 1.64-1.67 (m, 1H), 1.75-1.85 (m, 2H), 1.96-2.06 (m, 4H), 2.16-2.22 (m, 1H), 2.60-2.72 (m, 2H), 2.80-2.87 (m, 4H), 4.93 (s, 1H), 6.396 (d, J=2.8 Hz, 1H), 6.45 (dd, J=8.4, 2.8 Hz, 1H), 6.91 (d, J=8.4 Hz, 1H), 7.06 (d, J=7.6 Hz, 1H), 7.13 (d, J=7.6 Hz, 1H), 7.24 (s, 1H), 8.93 (s, 1H); $^{13}$C NMR (100 MHz, DMSO) δ 14.96, 23.82, 25.14, 26.01, 27.19, 29.18, 31.88, 32.44, 33.31, 37.84, 43.10, 46.39 (2×), 47.61, 84.40, 112.59, 114.81, 122.41, 123.45, 125.33, 125.90, 130.40, 137.05, 141.16, 141.96, 145.27, 154.83; IR(CCl4) ν 3609, 3259, 2913, 2869, 2855, 1722, 1612, 1499, 1287, 1249, 1068, 1053, 1029, 1011, 820 cm$^{-1}$; MS (EI) 388 (5), 370 (4), 228 (6), 173 (7), 149 (10), 111 (8), 84 (98), 66 (100); HRMS (EI) calculated for C$_{27}$H$_{32}$O$_2$ 388.240231. Found 388.239602.

Example 4

PN228: 17α-(2,2-Diacetyl-1,3-dihydro-2H-inden-5-yl)-estradiol

17α-Ethynylestradiol (0.5 mmol, 150 mg), 3,3-(diprop-2-ynyl)-2,4-pentadione (0.6 mmol, 105.6 mg), RhCl(PPh3)3 (0.05 mmol, 46 mg). Column chromatography on silica gel (2/1 hexan/EtOAc) yielded 119 mg (50%) of a colorless compound.

The colorless solid compound. M.p. 158° C.; [α]D=+40.9° (c 0.0055 g/ml, acetone); $^1$H NMR (400 MHz, C6D6) δ 0.71-0.78 (m, 1H), 1.04 (s, 3H), 1.05-1.19 (m, 1H), 1.30-1.40 (m, 4H), 1.62-1.65 (m, 2H), 1.69 (s, 3H), 1.70 (s, 3H), 1.72-1.77 (m, 2H), 1.90-1.96 (m, 2H), 2.21-2.27 (m, 1H), 2.60-2.70 (m, 2H), 3.22-3.34 (m, 4H), 4.46 (s, 1H), 6.39 (d, J=2.4 Hz, 1H), 6.47 (dd, J=8 Hz, 2.4, 1H), 6.92 (d, J=8 Hz, 1H), 6.99 (d, J=8 Hz, 1H), 7.18 (s, 1H) signal overlapped, 7.32 (s, 1H); $^{13}$C NMR (100 MHz, C6D6) δ 15.71, 25.08, 26.60, 26.66, 27.38, 28.50, 30.61, 34.74, 38.01, 38.39, 39.75, 40.52, 44.31, 47.87, 49.20, 75.75, 86.55, 113.69, 116.18, 124.00, 124.59, 127.37, 128.25, 129.24, 133.01, 138.53, 139.30, 140.03, 146.59, 154.96, 204.48 (2×); IR (ATR ZnSe) ν 3427, 2927, 2870, 1692, 1610, 1498, 1359, 1249, 1150 cm$^{-1}$; MS (EI) 472 (9), 454 (12), 411 (100), 228 (14), 213 (13), 159 (17); HRMS (EI) calculated for C$_{31}$H$_{36}$O$_4$ 472.261360. Found 472.261119.

Example 5

PN229: 17α-(1,3-Dihydro-2-tosyl-2H-indol-5-yl)-estradiol

17α-Ethynylestradiol (0.5 mmol, 150 mg), N,N-di(prop-2-ynyl)-4-methylbenzenesulphonylamide (0.6 mmol, 148 mg), RhCl(PPh3)3 (0.05 mmol, 46 mg). Column chromatography on silica gel (2/1 hexan/EtOAc) yielded (27%) of a colorless compound.

M.p. 178° C.; [α]D=+18.2° (c 0.00825 g/ml, acetone); $^1$H NMR (400 MHz, CD3OD) δ 0.42-0.47 (m, 1H), 1.02 (s, 3H), 1.14-1.37 (m, 5H), 1.45-1.67 (m, 3H), 1.83-1.95 (m, 3H), 2.27-2.40, (m, 1H), 2.31 (s, 3H), 2.62-2.73 (m, 2H), 4.56-4.60 (m, 4H), 6.41 (d, J=2.4 Hz, 1H), 6.46 (dd, J=8.4, 2.4 Hz, 1H), 6.87 (d, J=8.4 Hz, 1H), 7.14 (d, J=8 Hz, 1H), 7.23-7.32 (m, 2H), 7.72-7.75 (m, 4H); $^{13}$C NMR (100 MHz, CD3OD) δ 15.51, 21.46, 24.99, 27.41, 28.67, 30.64, 34.87, 38.86, 41.08, 44.76, 48.02, 54.67, 54.97, 55.68, 86.72, 113.60, 115.98, 122.16, 122.82, 127.10, 128.47, 128.74 (2×), 130.93 (2×), 132.40, 134.74, 135.59, 136.31, 138.71, 145.35, 147.93, 155.86; IR (ATR ZnSe) ν 3452, 3281, 2927, 2870, 1613, 1502, 1347, 1166, 1099, 818, 666 cm$^{-1}$; MS (FAB) $C_{33}H_{37}NO_4S$ the molecule peak is too weak for HRMS, FAB+ 544 (25), 526 (23), 456 (23), 443 (27), 401 (31), 339 (44), 211 (57), 165 (71), 91 (100).

Example 6

PN232:
17α-(1,3-Dihydroisobenzofuran-5-yl)-estradiol

17α-Ethynylestradiol (0.5 mmol, 150 mg), dipropargylether (0.6 mmol, 62 μl), RhCl(PPh3)3 (0.05 mmol, 46 mg). Column chromatography on silica gel (2/1 hexane/EtOAc) yielded 28 mg (14%) of a colorless compound.

M.p. 195° C.; [α]D=+44.8° (c 0.0125 g/ml, acetone); $^1$H NMR (400 MHz, CD3OD) δ 0.54-0.64 (m, 1H), 1.07 (s, 3H), 1.21-1.54 (m, 4H), 1.55-1.80 (m, 3H), 1.89-2.07 (m, 3H), 2.15-2.22 (m, 1H), 2.34-2.39 (m, 1H), 2.71-2.77 (m, 2H), 5.07 (m, 4H), 6.43 (d, J=2.8 Hz, 1H), 6.47 (dd, J=8.4 Hz, 1H), 6.93 (d, J=8.4 Hz, 1H), 7.20 (d, J=8.4 Hz, 1H), 7.30 (s, 1H), 7.32 (s, 1H); $^{13}$C NMR (100 MHz, CD3OD) δ 15.56, 25.05, 27.53, 28.74, 30.69, 34.94, 38.98, 41.16, 44.86, 48.06, 55.68, 74.20, 74.45, 86.87, 113.63, 115.98, 120.47, 121.18, 127.09, 128.11, 132.50, 138.38, 138.73, 139.10, 147.42, 155.86; IR (ATR ZnSe) ν 3417, 2930, 2866, 1723, 1613, 1502, 1287, 1252, 1027 cm$^{-1}$; MS (EI) 390 (2), 372 (3), 357 (2), 314 (7), 213 (20), 149 (50), 57 (63), 43 (100); HRMS (EI) calculated for $C_{26}H_{30}O_3$ 390.219495. Found 390.217671.

Example 7

PN233: 17α-[2-Cyano-2-(ethoxycarbonyl)-1,3-dihydro-2H-inden-5-yl]-estradiol

17α-Ethynylestradiol (0.5 mmol, 150 mg), ethyl 2-cyano-2-(prop-2-ynyl)pent-4-ynoate (0.6 mmol, 114 mg), RhCl(PPh3)3 (0.05 mmol, 46 mg). Column chromatography on silica gel (2/1 hexane/EtOAc) yielded 110 mg (45%) of a diastereoisomer mixture as a colorless compound.

M.p. 138° C.; [α]D=+21.4° (c 0.0055 g/ml, acetone); $^1$H NMR (400 MHz, CD3OD) δ 0.58-0.67 (m, 2×1H), 0.97 (s, 3H), 1.08 (s, 3H), 1.31 (t, J=7.2 Hz, 3H), 1.32 (t, J=7.2 Hz, 3H), 1.34-1.48 (m, 2×4H), 1.55-1.78 (m, 2×3H), 1.81-1.99 (m, 2×2H), 2.12-2.28 (m, 2×2H), 2.07 (s, 1H), 2.24 (s, 1H), 2.32-2.41 (m, 2×1H), 2.74-2.79 (m, 2×2H), 3.52-3.74 (m, 2×4H), 4.28 (q, J=7.2 Hz, 2H), 4.30 (q, J=7.2 Hz, 2H), 4.85 (bs, 2×1H), 6.44 (d, J=2.8 Hz, 1H), 6.47 (d, J=2 Hz, 1H), 6.48 (dd, J=8.4, 2.8 Hz, 1H), 6.51 (dd, J=8.4, 2.8 Hz, 1H), 6.95 (d, J=8.4 Hz, 1H), 7.03 (d, J=8.4 Hz, 1H), 7.06-7.12 (m, 2H), 7.21-7.35 (m, 4H); $^{13}$C NMR (100 MHz, CD3OD) δ 14.24, 14.54, 14.71, 15.54, 24.57 (2×), 27.60, 28.59, 28.74, 28.79 (2×), 30.73 (2×), 34.94 (2×), 35.68 (2×), 38.96 (2×), 40.86, 41.21, 43.89, 44.24 (2×), 44.88, 44.92 (2×), 46.45 (2×), 48.06, 64.15 (2×), 86.79, 86.84, 92.02 (2×), 113.66, 113.72, 115.98, 116.05, 121.90 (2×), 123.96, 124.72, 124.82, 127.11 (2×), 128.27, 128.40, 132.30, 132.52, 138.00 (2×), 138.68, 138.74, 138.79, 147.77 (2×), 155.88, 155.98, 169.92 (2×); IR (ATR ZnSe) ν 3376, 2927, 2866, 2249, 1736, 1727, 1499, 1442, 1283, 1226, 1059, 1011, 818 cm$^{-1}$; HRMS (FAB) calculated for $C_{31}H_{35}NO_4$ 485.256609. Found 485.258821.

Examples 8 to 12

The Other Compounds According to the Invention

Likewise, the compounds listed in the following table may be prepared using the method according to the invention:

| Example No. | X | $R^4$ | $R^5$ | MW |
| --- | --- | --- | --- | --- |
| 8 | $CH_2$ | H | Me | 402.57 |
| 9 | $C(COOEt)_2$ | H | Me | 546.69 |
| 10 | O | H | Me | 404.54 |
| 11 | $C(Me)_2$ | H | H | 416.59 |
| 12 | $C(Me)_2$ | H | Me | 430.62 |

Example 13

In Vitro Testing of Selectivity and Potency of Selected Novel Ligands in Reporter Assays The activity of some of the selected novel ligands of estrogen receptors was determined in reporter assays with the COS-7 cells. The reporter assay has an advantage over a classical determination of the ligand binding affinity for the receptor because in the case of steroid hormone receptors the high affinity of the ligand for the receptor doesn't always result in the equally high potency of activating the transcription via the receptor. The COS-7 cell line provides a significant advantage for this type of experiment, since it doesn't express endogenous ERα or ERβ at significant levels, and therefore it is highly suitable for the reporter assays. In addition, these compounds were also tested in the reporter assays with HEK293 cell-line.

COS-7 cells were transfected with the expression vector encoding human ERα or ERβ and with the reporter vector containing one estrogen responsive element followed by the minimal thymidine kinase promoter from the herpes simples virus. Luciferase was used as a reporter gene. The cells were seeded in a white 96-well plate after transfection, and were further cultivated in the DMEM medium without phenol red containing 2 mM glutamine, 20 mM Hepes, pH 7.5, 5 μg/ml insulin, 5 μg/ml human transferine, 100 μg/ml bovine serum albumin (BSA). Serially diluted compounds in DMSO were added to cells 24 hours after transfection, and after the next 24 hours the luciferase activity was measured using the commercial STEADY-GLO Luciferase Assay Kit (Promega) according to the manufacturer's instructions. The luminescence was measured using the combined spectrophotometer ENVISION (PerkinElmer) with 1 s signal integration. Data were evaluated with GraphPad Prism software and EC50 values (see Table 1) were calculated using a regression function (dose response, variable slope). The ligand selectivity for the given receptor was calculated as a ratio of relative activities of ERα and ERβ for the given ligand. The selectivity values are listed in Table 2, and the transcriptional activities in relation to the concentration of the ligand are shown in FIGS. 1-7.

TABLE 1

EC50 [nM] of tested ligands in the reporter assays

| Ligand | ER α | ER β |
|---|---|---|
| E2 | 0.66 | 1.80 |
| PN202 | 3.85 | 19.30 |
| PN207 | 2.49 | 14.50 |
| PN214 | 21.10 | 1.08 |
| PN228 | 18.97 | 60.39 |
| PN229 | 5.37 | 62.71 |
| PN232 | 5.14 | 12.09 |
| PN233 | 0.80 | 12.79 |

TABLE 2

The ligand selectivity for ERα and ERβ in the reporter assays

| Ligand | ER α | ER β |
|---|---|---|
| E2 | 1.00 | 1.00 |
| PN202 | 1.83 | 0.55 |
| PN207 | 2.13 | 0.47 |
| PN214 | 0.02 | 53.44 |
| PN228 | 1.16 | 0.86 |
| PN229 | 4.27 | 0.23 |
| PN232 | 0.86 | 1.16 |
| PN233 | 5.87 | 0.17 |

From EC50 values shown above it is evident that novel compounds are highly potent ligands of both of the estrogen receptors and their potency is comparable or very similar to that of estradiol. This is an important property, since these compounds are active in very low concentrations and their application is not associated with side effects, such as non-specific binding and cross-reactivity with other members of the nuclear receptor family, the interference with the metabolism of steroid compounds, or the general toxicity of the compounds in the body. The compounds PN202, PN207, PN214, PN229, PN232 and PN233 seem to be preferable ligands and the compounds PN214 and PN233 seem to be the most preferable ligands.

Moreover, the novel compounds exhibit different selectivity to one of the estrogen receptors. Here, the compounds PN229 and PN233 seem to be preferable selective ligands for ERα and the compound PN214 seem to be preferable selective ligands for ERβ. The compound PN214 is the most preferable selective ligand for ERβ, and the selectivity of this ligand is comparable to the best known selective ligands for this receptor.

Example 14

Test of Activity of Selected Novel Ligands in the Proliferation Assay

The MCF-7 cell line was derived from a breast adenocarcinoma and, considering its growth dependency on estrogen, it is a valuable tool for evaluation of estrogenic properties of chemical compounds. Since MCF-7 cells express exclusively ERα, the proliferative effect of tested compounds is mediated mainly by this receptor.

Figure 8:
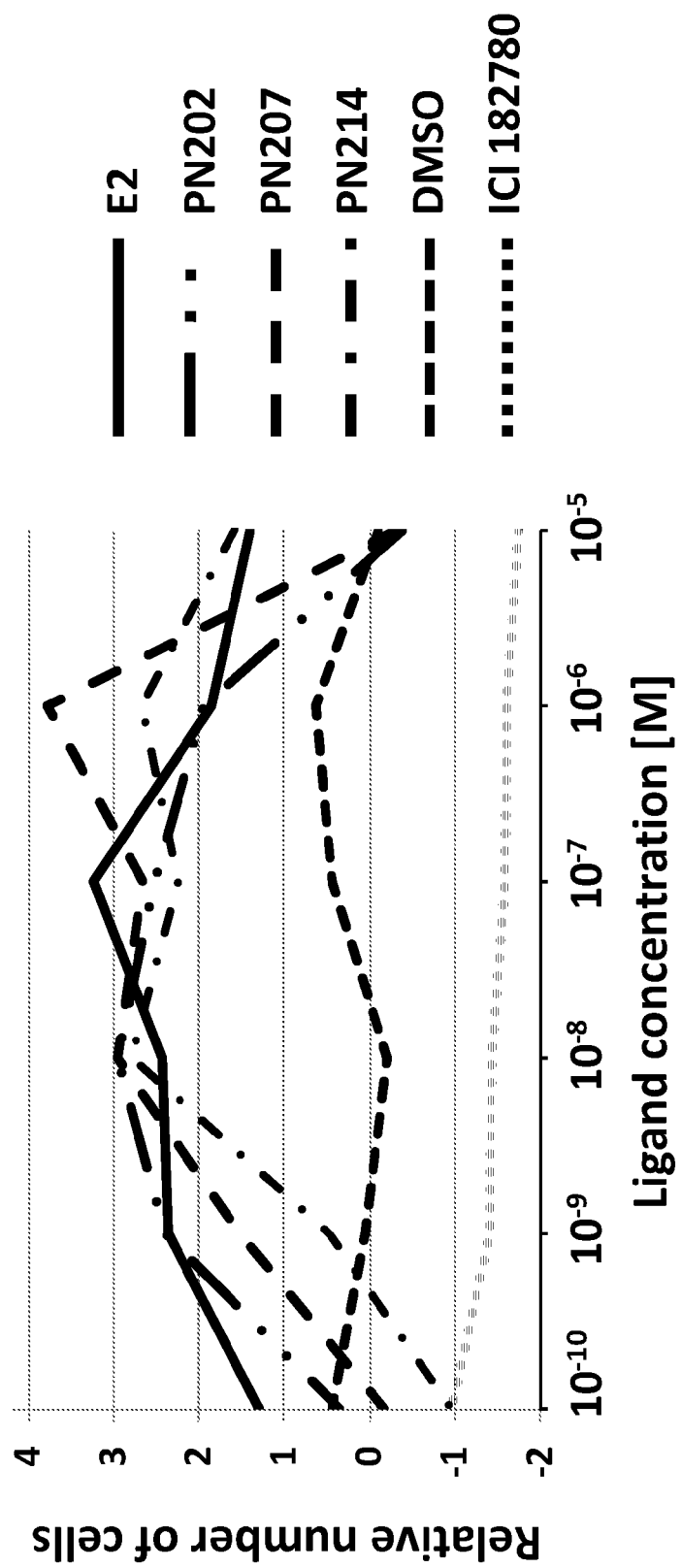
FIG. 8 graphically depicts the proliferation of estrogen-growth-dependent MCF-7 cell line in relationship to the concentration of E2, tested compounds and ICI 182 780.
Figure 9:
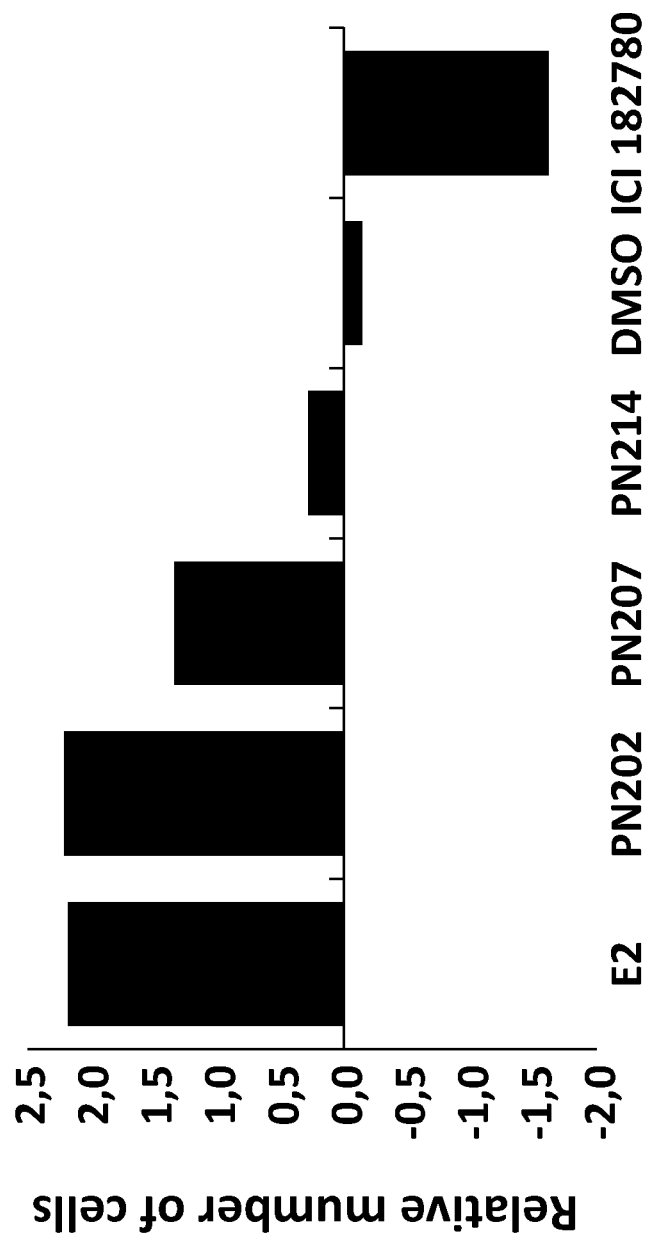
FIG. 9 graphically depicts the proliferation of estrogen-growth-dependent MCF-7 cell line in the presence of 1 nM E2 or tested compound.

MCF-7 cells were cultivated for 6 days in DMEM medium without phenol red containing 8% charcoal treated fetal calf serum and 2 mM glutamine. During this time the cells stopped proliferating and the medium was supplemented with different concentrations of tested compounds in DMSO. The cells were further cultured in the medium described above in the presence of tested compounds, and after 3 days the medium was changed and the tested compounds in DMSO were added to the medium once again. After another 3 days the amount of viable cells was measured using the kit CELL-TITER-BLUE Cell Viability Assay (Promega) according to the manufacturer's instructions. The fluorescent measurement was carried out on the combined spectrophotometer ENVISION (PerkinElmer), and the results are shown in FIGS. 8 and 9.

The data show that there is there is a toxic effect exerted both by the natural ligand estradiol and by the tested compounds in the range of high concentrations of ligands (1-10 µM). On the other hand, in the concentration range 0.5 nM to 100 nM, corresponding to the natural levels of estradiol in the body, the compounds according to the invention stimulate proliferation of MCF 7 cells. In the concentration range of 10 to 100 nM, the proliferation effect of all tested compounds is comparable to that of estradiol. In the 1 nM concentration, the proliferation effect of PN202 is comparable to estradiol whereas PN214 shows no activity. This finding is fully in agreement with the data from the reporter assays wherein 1 nM PN214 is ERβ selective and doesn't stimulate ERα in this concentration. As mentioned above, the proliferation effect caused by estrogens in MCF-7 cells is mediated mainly by ERα, and the low MCF-7 cell proliferation in the presence of 1 nM PN214 supports the finding that this compound is a highly selective ligand.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

The cited patents, patent application publications, and publications listed bellow are hereby incorporated herein by reference in their entirety.

Cited Patent Literature
  GB 2361642 A
  WO 00/53620
  WO 05/048956
  WO 05/099704
  WO 2006/013196
  US 2007/0135400 A1
  EP1131 336

Cited Non-Patent Literature
1. Greene, G. L. et al. Sequence and expression of human estrogen receptor complementary DNA. *Science* 231, 1150-4 (1986).

2. Green, S. et al. Human oestrogen receptor cDNA: sequence, expression and homology to verb-A. *Nature* 320, 134-9 (1986).
3. Lubahn, D. B. et al. Alteration of reproductive function but not prenatal sexual development after insertional disruption of the mouse estrogen receptor gene. *Proc Natl Acad Sci USA* 90, 11162-6 (1993).
4. Hewitt, S. C. & Korach, K. S. Oestrogen receptor knockout mice: roles for oestrogen receptors alpha and beta in reproductive tissues. *Reproduction* 125, 143-9 (2003).
5. Kuiper, G. G., Enmark, E., Pelto-Huikko, M., Nilsson, S. & Gustafsson, J. A. Cloning of a novel receptor expressed in rat prostate and ovary. *Proc Natl Acad Sci USA* 93, 5925-30 (1996).
6. Gustafsson, J. A. Estrogen receptor beta—a new dimension in estrogen mechanism of action. *J Endocrinol* 163, 379-83 (1999).
7. Ogawa, S. et al. The complete primary structure of human estrogen receptor beta (hER beta) and its heterodimerization with ER alpha in vivo and in vitro. *Biochem Biophys Res Commun* 243, 122-6 (1998).
8. Meyers, M. J. et al. Estrogen receptor-beta potency-selective ligands: structure-activity relationship studies of diarylpropionitriles and their acetylene and polar analogues. *J Med Chem* 44, 4230-51 (2001).
9. Malamas, M. S. et al. Design and synthesis of aryl diphenolic azoles as potent and selective estrogen receptor-beta ligands. *J Med Chem* 47, 5021-40 (2004).
10. Mewshaw, R. E. et al. ERbeta ligands. 3. Exploiting two binding orientations of the 2-phenylnaphthalene scaffold to achieve ERbeta selectivity. *J Med Chem* 48, 3953-79 (2005).
11. Hillisch, A. et al. Dissecting physiological roles of estrogen receptor alpha and beta with potent selective ligands from structure-based design. *Mol Endocrinol* 18, 1599-609 (2004).
12. Couse, J. F. & Korach, K. S. Estrogen receptor null mice: what have we learned and where will they lead us? *Endocr Rev* 20, 358-417 (1999).
13. Gustafsson, J. A. What pharmacologists can learn from recent advances in estrogen signalling. *Trends Pharmacol Sci* 24, 479-85 (2003).
14. Harris, H. A. Estrogen receptor-beta: recent lessons from in vivo studies. *Mol Endocrinol* 21, 113 (2007).
15. Koehler, K. F., Helguero, L. A., Haldosen, L. A., Warner, M. & Gustafsson, J. A. Reflections on the discovery and significance of estrogen receptor beta. *Endocr Rev* 26, 465-78 (2005).
16. Palmieri, C. et al. Estrogen receptor beta in breast cancer. *Endocr Relat Cancer* 9, 1-13 (2002).
17. Mann, S. et al. Estrogen receptor beta expression in invasive breast cancer. *Hum Pathol* 32, 113-8 (2001).
18. Omoto, Y. et al. Clinical value of the wild-type estrogen receptor beta expression in breast cancer. *Cancer Lett* 163, 207-12 (2001).
19. Weihua, Z. et al. A role for estrogen receptor beta in the regulation of growth of the ventral prostate. *Proc Natl Acad Sci USA* 98, 6330-5 (2001).
20. Imamov, O. et al. Estrogen receptor beta regulates epithelial cellular differentiation in the mouse ventral prostate. *Proc Natl Acad Sci USA* 101, 9375-80 (2004).
21. Neubauer, B. L. et al. The selective estrogen receptor modulator trioxifene (LY133314) inhibits metastasis and extends survival in the PAIII rat prostatic carcinoma model. *Cancer Res* 63, 6056-62 (2003).
22. Pearce, S. T. & Jordan, V. C. The biological role of estrogen receptors alpha and beta in cancer. *Crit. Rev Oncol Hematol* 50, 3-22 (2004).
23. Korte, T. et al. Female mice lacking estrogen receptor beta display prolonged ventricular repolarization and reduced ventricular automaticity after myocardial infarction. *Circulation* 111, 2282-90 (2005).
24. Pelzer, T. et al. Increased mortality and aggravation of heart failure in estrogen receptor-beta knockout mice after myocardial infarction. *Circulation* 111, 1492-8 (2005).
25. Zhu, Y. et al. Abnormal vascular function and hypertension in mice deficient in estrogen receptor beta. *Science* 295, 505-8 (2002).
26. Skavdahl, M. et al. Estrogen receptor-beta mediates male-female differences in the development of pressure overload hypertrophy. *Am J Physiol Heart Circ Physiol* 288, H469-76 (2005).
27. Shughrue, P. J., Lane, M. V. & Merchenthaler, I. Comparative distribution of estrogen receptor-alpha and -beta mRNA in the rat central nervous system. *J Comp Neurol* 388, 507-25 (1997).
28. Gundlah, C. et al. Estrogen receptor-beta regulates tryptophan hydroxylase-1 expression in the murine midbrain raphe. *Biol Psychiatry* 57, 938-42 (2005).
29. Walf, A. A., Rhodes, M. E. & Frye, C. A. Antidepressant effects of ERbeta-selective estrogen receptor modulators in the forced swim test. *Pharmacol Biochem Behav* 78, 523-9 (2004).
30. Shively, C. A., Mirkes, S. J., Lu, N. Z., Henderson, J. A. & Bethea, C. L. Soy and social stress affect serotonin neurotransmission in primates. *Pharmacogenomics J* 3, 114-21 (2003).
31. Rocha, B. A., Fleischer, R., Schaeffer, J. M., Rohrer, S. P. & Hickey, G. J. 17 Beta-estradiol-induced antidepressant-like effect in the forced swim test is absent in estrogen receptor-beta knockout (BERKO) mice. *Psychopharmacology* (Berl) 179, 637-43 (2005).
32. Krezel, W., Dupont, S., Krust, A., Chambon, P. & Chapman, P. F. Increased anxiety and synaptic plasticity in estrogen receptor beta-deficient mice. *Proc Natl Acad Sci USA* 98, 12278-82 (2001).
33. Imwalle, D. B., Gustafsson, J. A. & Rissman, E. F. Lack of functional estrogen receptor beta influences anxiety behavior and serotonin content in female mice. *Physiol Behav* 84, 157-63 (2005).
34. Walf, A. A. & Frye, C. A. ERbeta-selective estrogen receptor modulators produce antianxiety behavior when administered systemically to ovariectomized rats. *Neuropsychopharmacology* 30, 1598-609 (2005).
35. Lund, T. D., Rovis, T., Chung, W. C. & Handa, R. J. Novel actions of estrogen receptor-beta on anxiety-related behaviors. *Endocrinology* 146, 797-807 (2005).
36. Day, M., Sung, A., Logue, S., Bowlby, M. & Arias, R. Beta estrogen receptor knockout (BERKO) mice present attenuated hippocampal CA1 long-term potentiation and related memory deficits in contextual fear conditioning. *Behav Brain Res* 164, 128-31 (2005).
37. Wang, L., Andersson, S., Warner, M. & Gustafsson, J. A. Morphological abnormalities in the brains of estrogen receptor beta knockout mice. *Proc Natl Acad Sci USA* 98, 2792-6 (2001).
38. Wang, L., Andersson, S., Warner, M. & Gustafsson, J. A. Estrogen receptor (ER)beta knockout mice reveal a role for ERbeta in migration of cortical neurons in the developing brain. *Proc Natl Acad Sci USA* 100, 703-8 (2003).
39. Taurog, J. D. et al. Inflammatory disease in HLA-B27 transgenic rats. *Immunol Rev* 169, 209-23 (1999).

40. Harris, H. A. et al. Evaluation of an estrogen receptor-beta agonist in animal models of human disease. *Endocrinology* 144, 4241-9 (2003).
41. Chadwick, C. C. et al. Identification of pathway-selective estrogen receptor ligands that inhibit NF-kappaB transcriptional activity. *Proc Natl Acad Sci USA* 102, 2543-8 (2005).
42. Cristofaro, P. A. et al. WAY-202196, a selective estrogen receptor-beta agonist, protects against death in experimental septic shock. *Crit. Care Med* 34, 2188-93 (2006).
43. Harris, H. A., Bruner-Tran, K. L., Zhang, X., Osteen, K. G. & Lyttle, C. R. A selective estrogen receptor-beta agonist causes lesion regression in an experimentally induced model of endometriosis. *Hum Reprod* 20, 936-41 (2005).
44. Cvoro, A. et al. Selective estrogen receptor-beta agonists repress transcription of proinflammatory genes. *J Immunol* 180, 630-6 (2008).
45. Follettie, M. T. et al. Organ messenger ribonucleic acid and plasma proteome changes in the adjuvant-induced arthritis model: responses to disease induction and therapy with the estrogen receptor-beta selective agonist ERB-041. *Endocrinology* 147, 714-23 (2006).
46. Shim, G. J. et al. Disruption of the estrogen receptor beta gene in mice causes myeloproliferative disease resembling chronic myeloid leukemia with lymphoid blast crisis. *Proc Natl Acad Sci USA* 100, 6694-9 (2003).
47. Imamov, O., Shim, G. J., Warner, M. & Gustafsson, J. A. Estrogen receptor beta in health and disease. *Biol Reprod* 73, 866-71 (2005).
48. Witte, D., Chirala, M., Younes, A., Li, Y. & Younes, M. Estrogen receptor beta is expressed in human colorectal adenocarcinoma. *Hum Pathol* 32, 940-4 (2001).
49. Foley, E. F., Jazaeri, A. A., Shupnik, M. A., Jazaeri, O. & Rice, L. W. Selective loss of estrogen receptor beta in malignant human colon. *Cancer Res* 60, 245-8 (2000).
50. Hulley, S. et al. Noncardiovascular disease outcomes during 6.8 years of hormone therapy: Heart and Estrogen/progestin Replacement Study follow-up (HERS II). *JAMA* 288, 58-66 (2002).
51. Grodstein, F., Newcomb, P. A. & Stampfer, M. J. Postmenopausal hormone therapy and the risk of colorectal cancer: a review and meta-analysis. *Am J Med* 106, 574-82 (1999).
52. Campbell-Thompson, M., Lynch, I. J. & Bhardwaj, B. Expression of estrogen receptor (ER) subtypes and ERbeta isoforms in colon cancer. *Cancer Res* 61, 632-40 (2001).
53. Peters, R. H., Crowe, D. F., Avery, M. A., Chong, W. K. & Tanabe, M. 11 beta-nitrate estrane analogues: potent estrogens. *J Med Chem* 32, 2306-10 (1989).
54. Jaouen, G. & Vessiers, A. in Eur. Pat. Appl. (1989).
55. Foy, N., Stephan, E. & Jaouen, G. Soft cleavage of THP protected estradiols mediated by TMSI. *Journal of Chemical Research (Synopses)* 2001, 518-519 (2001).
56. Stéphan, E., Affergan, T., Weber, P. & Jaouen, G. *Tetrahedron Lett.* 39, 9427-9430 (1998).
57. Foy, N., Stéphan, E. & Jaouen, G. *Tetrahedron Lett.* 41, 8089-8092 (2000).
58. Foy, N. et al. Synthesis, receptor binding, molecular modeling, and proliferative assays of a series of 17alpha-arylestradiols. *Chembiochem* 4, 494-503 (2003).
59. Gennaro, A. R. et al. Remington: The Science and Practice in Pharmacy. 20th Edition. Lippincot Williams & Wilkins, Baltimore, Md., 2000.
60. Chalabala, M. et al. Technologie Lék ů Galén, Praha, 2001.
61. Kibbe, A. H. Handbook of Pharmaceutical Excipients. Pharmaceutical Press, London, 2000.

What is claimed is:

1. A compound of general formula II

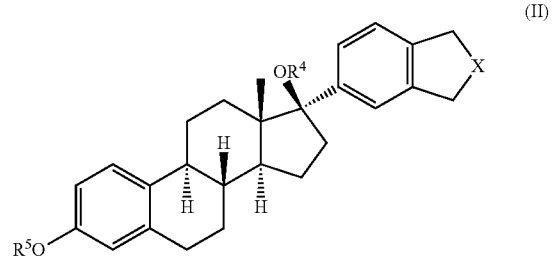

wherein

X is C or heteroatom selected from the group consisting of N, O, S, wherein X optionally carries one or two substituents independently selected from the group consisting of alkyl, aryl, carboxyl, esierified carboxyl, hydrogencarbonyl, alkylcarbonyl and nitrite groups, or X is p-toluensulphoamido (NTs)

$R^4$ is H or alkyl: and $R^5$ is H, alkyl, aryl, or acyl, or isomeric forms or salts thereof.

2. The compound according to claim 1, selected from the following compounds:

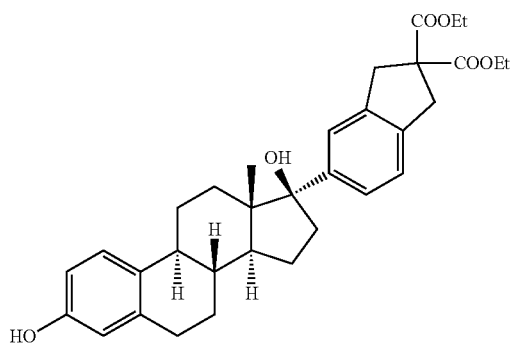

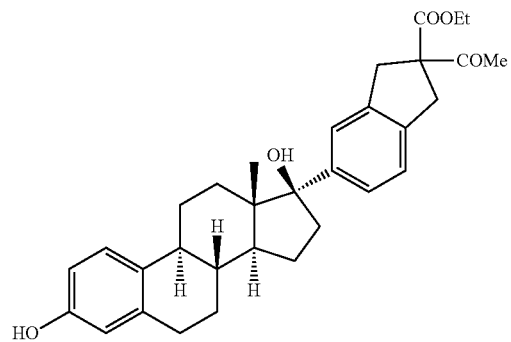

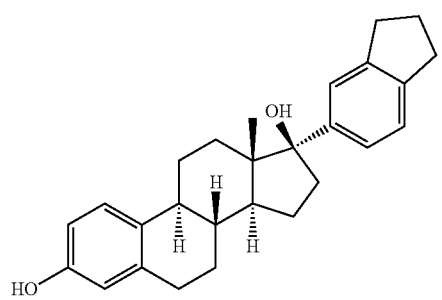

PN214

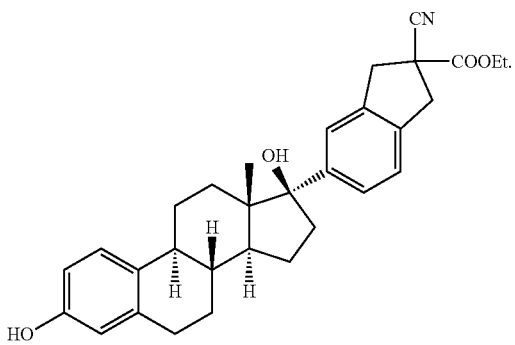

PN233

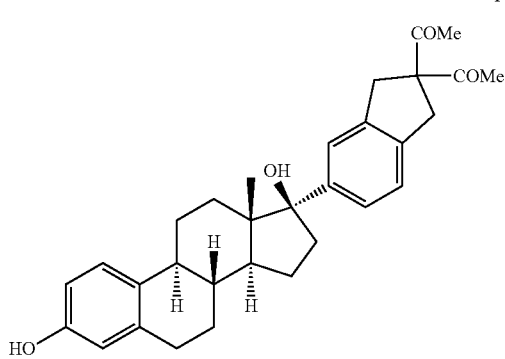

PN228

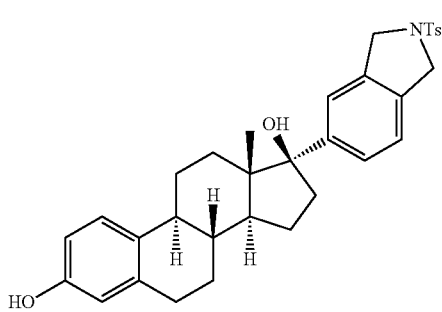

PN229

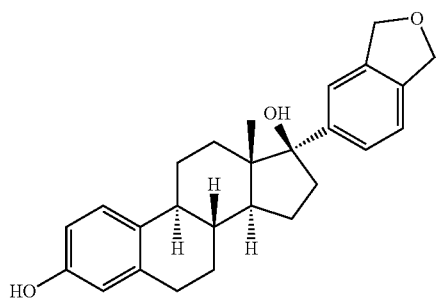

PN232 and

3. The compound according to claim 2, selected from the compounds of formulas PN214, PN229, and PN233 mentioned in claim 2.

4. A medicament, comprising:
the compound of claim 1.

5. A pharmaceutical composition, comprising:
the compound of claim 1, optionally further comprising pharmaceutically acceptable excipients.

6. A method of the preparation of the compound according to claim 1, comprising cyclotrimerization of ethynylestradiol in an organic solvent with the diyne of the general formula III

(III)

wherein X is as defined in claim 1, under the addition of a catalyst in the form of a transition metal complex, and optionally removing the solvent and purifying the product.

7. The method according to claim 6, wherein ethynylestradiol is 17α-ethynylestradiol; and/or
the organic solvent is selected from toluene, benzene, THF, dichloromethane, acetonitrile, and mixtures thereof; and/or
the catalyst is selected from transition metal complexes.

8. The method according to claim 6, wherein
the molar ratio of ethynylestradiol to diynes of the formula III is approximately 2:1 to 1:5; and/or
the reaction is carried out under stirring; and/or
the reaction is carried out for 8 to 72 hours.

9. A method according to claim 7, wherein the organic solvent is toluene or acetonitrile or a mixture thereof.

10. A method according to claim 7, wherein the-transition metal complexes are selected from the group consisting of Ru, Rh, Co, Ni complexes, and combinations thereof.

11. A method according to claim 10, wherein the transition metal complexes are selected from the group consisting of Ni(cod)$_2$/PPh$_3$ and RhCl(PPh$_3$)$_3$.

12. A method according to claim 8, wherein the molar ratio of ethynylestradiol to diynes of the formula III is approximately 1:1 to 1:2.

13. A method according to claim 12, wherein the molar ratio of ethynylestradiol to diynes of the formula III is approximately 1:1.2.

14. A method according to claim 8, wherein the reaction is carried out under stirring at 15 to 100° C.

15. A method according to claim 14, wherein the reaction is carried out under stirring at 15 to 60° C.

16. A method according to claim 15, wherein the reaction is carried out under stirring at 20° C.

17. A method according to claim 8, wherein the reaction is carried out for 24 to 48 hours.

18. A method according to claim 8, wherein the reaction is carried out until the starting compounds are completely consumed.

* * * * *

UNITED STATES PATENT AND TRADEMARK OFFICE
CERTIFICATE OF CORRECTION

PATENT NO. : 8,334,280 B2  Page 1 of 1
APPLICATION NO. : 12/990826
DATED : December 18, 2012
INVENTOR(S) : Petr Novak et al.

It is certified that error appears in the above-identified patent and that said Letters Patent is hereby corrected as shown below:

In the title page:
(75) Inventors:
"Petr Novak, Havlichkuv Brod (CZ)" should read --Petr Novak, Havlickuv Brod (CZ)--.

(30) Foreign Application Priority Data:
"(CV)" should read --(CZ)--.

In the specification:
Col. 18, line 59
"cial STEADY-GLO Luciferase Assay Kit (Promega) accord-" should read
--cial STEADY-GLO® Luciferase Assay Kit (Promega) accord- --.

In the claims:
Col. 24, lines 22-23
"ing of alkyl, aryl, carboxyl, esierfied carboxyl, hydrogencarbonyl, alkylcarbonyl and nitrite groups, or X is" should read --ing of alkyl, aryl, carboxyl, esterified carboxyl, hydrogencarbonyl, alkylcarbonyl and nitrile groups, or X is--.

Signed and Sealed this
Twenty-sixth Day of February, 2013

Teresa Stanek Rea
*Acting Director of the United States Patent and Trademark Office*